(12) United States Patent
Cooper et al.

(10) Patent No.: US 7,078,380 B2
(45) Date of Patent: Jul. 18, 2006

(54) ANTIBACTERIAL AGENTS COMPRISING CONJUGATES OF GLYCOPEPTIDES AND PEPTIDIC MEMBRANE ASSOCIATING ELEMENTS

(75) Inventors: Matthew Allister Cooper, Cambridge (GB); Jason Richard Betley, Bury St. Edmonds (GB)

(73) Assignees: Cambridge University Technical Services Limited, Cambridge (GB); Adprotech Limited, Essex (GB)

( * ) Notice: Subject to any disclaimer, the term of this patent is extended or adjusted under 35 U.S.C. 154(b) by 0 days.

(21) Appl. No.: 10/415,935

(22) PCT Filed: Nov. 2, 2001

(86) PCT No.: PCT/GB01/04867

§ 371 (c)(1),
(2), (4) Date: Nov. 3, 2003

(87) PCT Pub. No.: WO02/36612

PCT Pub. Date: May 10, 2002

(65) Prior Publication Data

US 2004/0106544 A1 Jun. 3, 2004

(30) Foreign Application Priority Data

Nov. 3, 2000 (GB) ................................. 0026924.1

(51) Int. Cl.
*A61K 38/00* (2006.01)
*A61K 38/02* (2006.01)
*A61K 38/20* (2006.01)
*A61K 38/12* (2006.01)

(52) U.S. Cl. .................... 514/2; 530/300; 530/327; 514/14; 514/8; 514/9

(58) Field of Classification Search ............... 530/322, 530/333; 514/8
See application file for complete search history.

(56) References Cited

U.S. PATENT DOCUMENTS 3,067,099 A    12/1962    McCormick et al.
4,698,327 A *  10/1987    Nagarajan et al. ............. 514/8

FOREIGN PATENT DOCUMENTS

| WO | WO 96/30401 | 10/1996 |
|----|-------------|---------|
| WO | WO 96/38163 | 12/1996 |
| WO | WO 98/00153 | 1/1998  |
| WO | WO 98/02454 | 1/1998  |
| WO | WO 98/52614 | 11/1998 |
| WO | WO 00/64487 | 11/2000 |
| WO | WO 01/76636 | 10/2001 |

OTHER PUBLICATIONS

A Malabarba, et al. Medicinal Research Reviews (1997) 17(1), 69-137.*
BCS Chia, et al. Eur. J. Biochem. (2000) 267, 1894-1908.*
L Zhang, et al. Biochemistry (2000) 39, 14504-14514.*
K Matsuzaki. Biochimica et Biophysica Acta (1999) 1462, 1-10.*
K Matsuzaki, et al. Biochemistry (1997) 36, 9799-9806.*
F Van Bambeke. Current Opinion in Pharmacology (2004) 4, 471-478.*
A King, et al. Journal of Antimicrobial Chemotherapy (2004) 53, 797-803.*
Gibson et al., "Bobinin-like Peptides with Antimicrobial Activity from Skin Secretions of the Asian Toad, *Bobina orientalis*", The Journal of Biological Chemistry, vol. 266, No. 34, pp 23103-23111 (1991).
Habermann, "Bee and Wasp Venoms", Science, vol. 177, pp. 314-322 (1972).
Latorre et al., "Voltage-Dependent Channels in Planar Lipid Bilayer Membranes", Physiological Reviews, vol. 61, No. 1, pp 77-150 (1981).
Sheldrick et al., "Structure of vancomycin and its complex with acetyl-D-alanyl-D-alanine", Nature, vol. 271, pp 223-225, (1978).
Arthur et al., "Characterization of Tn1546, a Tn3-Related Transposon Conferring Glycopeptide Resistance by Synthesis of Depsipeptide Peptidoglycan Precursors in *Ennterococcus faecium* BM4147", Journal of Bacteriology, vol. 175, No. 1, pp 117-127 (1993).
Dutka-Malen et al., "The VANA glycopeptide resistance protein is related to D-alanyl-D alanine ligase cell wall biosynthesis enzymes", Mol. Gen. Genet 224, pp 364-372 (1990).
Bugg et al., "Molecular Basis for Vancomycin Resistance in *Enterococcus faecium* BM4147: Biosynthesis of a Depsipeptide Peptidoglycan Precursor by Vancomycin Resistance Proteins VanH and VanA", Biochemistry, vol. 30, No. 43, pp 10408-10415 (1991).

(Continued)

Primary Examiner—Bruce R. Campell
Assistant Examiner—Andrew D. Kosar
(74) Attorney, Agent, or Firm—Harness, Dickey & Pierce, P.L.C.

(57) ABSTRACT

The invention concerns agents with anti-bacterial activity and methods and intermediates for their production. The present invention further concerns the use of such agents for the treatment of bacterial infections in animals, including man. The agents are derivatives of vancomycin-type antibiotics, of structure: V-L-W-X; wherein V is a glycopeptide moiety which inhibits peptidoglycan biosynthesis in bacteria; L is a linking group; W is a peptidic membrane-associating element such as an element based on naturally-occurring animal or bacterial peptide antibiotics; and X is hydrogen or a membrane-insertive element.

12 Claims, No Drawings

OTHER PUBLICATIONS

Evers et al., "Regulation of VanB-Type Vancomycin Resistance Gene Expression by the $VanS_B$-$VanR_B$ Two-Component Regulatory System in *Enterococcus faecalis* V583", Journal of Bacteriology, vol. 178, No. 5, pp 1302-1309 (1996).

Baptista et al., "Specificity of Induction of Glycopeptide Resistance Genes in *Enterococcus faecalis*", Antimicrobial Agents and Chemotherapy, vol. 40, No. 10, pp 2291-2295 (1996).

Billot-Klein et al., "Association constants for the binding of vancomycin and telcoplanin to N-acetyl-D-alanyl-D-alanine and N-acetyl-D-alanyl-D-serine", Biochemical Journal Letters, vol. 304, pp 1021-1022 (1994).

Reynolds et al., "Analysis of peptidoglycan precursors in vancomycin-resistant *Enterococcus gallinarum* BM4174", Biochem Journal, vol. 301, pp 5-8 (1994).

Handwerger et al., "Concomitant High-Level Vancomycin and Penicillin Resistance in Clinical Isolates of *Enterococci*", Clinical Infectious Diseases, vol. 14, pp 665-661 (1992).

Handwerger et al., "Nosocomial Outbreak Due to *Enterococcus faecium* Highly Resistant to Vancomycin, Penicillin, and Gentamicin", Clinical Infectious Diseases, vol. 16, pp 750-5 (1993).

Murray, "The Life and Times of the *Enterococcus*", Clinical Microbiology Reviews, vol. 3, No. 1, pp46-65 (1990).

Woodford et al., "Plasmid-Mediated vanB Glycopeptide Resistance in *Enterococci*", Microbial Drug Resistance, vol. 1, No. 3, pp 235-240 (1995).

Sundram et al., "General and Efficient Method for the Solution and Solid-Phase Synthesis of Vancomycin Carboxamide Derivatives", J. Org. Chem., vol. 60, pp 1102-1103 (1995).

Cooper et al., "Reductive Alkylation of Glycopeptide Antibiotics: Synthesis and Antibacterial Activity", The Journal of Antibiotics, vol. 49, No. 6, pp 575-581 (1996).

Rodriguez et al., "Novel Glycopeptide Antibiotics: N-Alkylated Derivatives Active Against Vancomycin-Resistant *Enterococci*", The Journal of Antibiotics, pp 560-569 (1998).

Dong et al., "Strategies for targeting complement inhibitors in ischaemia/reperfusion injury", Molecular Immunology, vol. 36, pp 957-963 (1999).

Ge et al., "Vancomycin Derivatives That Inhibit Peptidoglycan Biosynthesis Without Binding D-Ala-D-Ala", Science, vol. 284, pp 507-511 (1999).

Jack et al., "Natural Peptides with Antimicrobial Activity", Chimia, vol. 52, pp48-55 (1998).

McCafferty et al., "Synergy and duality in peptide antibiotic mechanisms", Chemical Biology, vol. 3, pp 672-680 (1999).

Dankert et al., "Biomedical Polymers: Bacterial Adhesion, Colonization, and Infection", CRC Critical Reviews in Biocompatibility, vol. 2, pp 219-301.

Kamal et al., "Reduced Intravascular Catheter Infection by Antibiotic Bonding", Jama, vol. 265, No. 18, pp 2364-2368 (1991).

Farber et al., "The Use of Nonsteroidal Antiinflammatory Drugs to Prevent Adherence of *Staphylococcus epidermidis* to Medical Polymers", The Journal of Infectious Diseases, vol. 166, pp 861-865 (1992).

Atherton et al., "Solid Phase Peptide Synthesis" IRL Press, Oxford, pp 31-32 & 47-61 (1989).

* cited by examiner

ANTIBACTERIAL AGENTS COMPRISING CONJUGATES OF GLYCOPEPTIDES AND PEPTIDIC MEMBRANE ASSOCIATING ELEMENTS

CROSS-REFERENCE TO RELATED APPLICATIONS

This application is a U.S. national stage filing under 35 U.S.C. § 371 of international application PCT/GB01/04867, filed Nov. 2, 2001, which claims priority of Great Britain application 0026924.1 filed Nov. 3, 2000.

The present invention concerns agents with anti-bacterial activity and methods and intermediates for their production. The present invention further concerns the use of such agents for the treatment of bacterial infections in animals, including man.

BACKGROUND OF THE INVENTION

Diseases caused by bacterial infections have significant morbidity and mortality in man and other mammals. The infection process consists of three stages: bacterial entry and colonization of the Host; bacterial invasion and growth in host tissues along with the appearance of toxic substances; and the host response.

Bacterial infections can be classed broadly into those caused by Gram positive bacteria, such as the Staphylococci and Streptococci, and those caused by Gram negative bacteria, such as *Escherichia coli*. Gram positive bacteria have a typical lipid bilayer cytoplasmic membrane surrounded by a rigid cell wall. The cell wall is composed mainly of peptidoglycan, a polymer of N-acetylglucosamine and N-acetyl muramic acid crosslinked by a peptide comprising alternating D- and L-amino acids. In addition, the outer cell wall of Gram-positive bacteria comprises a complex of polysaccharides, proteins, teichoic acids, and lipoteichoic acids. By contrast, Gram-negative bacteria have a much smaller peptidoglycan layer, an outer membrane that contains lipopolysaccharide which lacks the complex layer of carbohydrate and teichoic acids.

Antibiotics are substances produced by various species of microorganisms (bacteria, fungi) that suppress the growth of other microorganisms and may eventually destroy them. In addition, common usage extends the term antibiotic to include antibacterial agents which are semi-synthetic antibiotics, i.e. chemically modified bacterial antibiotics, as well as synthetic antibacterial agents (e.g. sulphonamides) which are not products of microbes. Also included in the term "antibiotic" are various peptides found in host defence systems which are produced locally in response to colonisation by or invasion of microorganisms (e.g. peptides produced by amphibians, including the peptide magainin). Hundreds of antibiotics have been identified, and many have been developed to the stage where they are of value in the therapy of infectious diseases.

Several schemes have been proposed to classify and group antimicrobial agents. The most common classification has been based on chemical structure and proposed mechanism of action, as follows: (1) agents that act directly on the cell membrane of the microorganism, affecting permeability and leading to leakage of the intracellular compounds, such as detergents, cationic peptides, gramicidin A, and pplymyxin; (2) agents that inhibit synthesis of bacterial cell walls and includes the beta-lactams, cephalosporins and glycopeptides; (3) agents that affect bacterial protein synthesis including tetracycline and chloramphenicol; (4) agents that act as antimetabolites and interfere with the bacterial synthesis of folic acid, such as the sulphonamides; and (5) agents that inhibit nucleic acid synthesis or activity such as quinolones.

Peptide anti-bacterial agents which act directly on the bacterial membrane cause a general permeabilisation or modification of the bacterial cytoplasmic membrane. This results from the binding of peptides to components of the outer membrane surface, causing reorganisation of membrane structure and the creation of pores through which the intracellular contents may leak. Generally, these features are associated with an amphiphilic peptide nature often including helical secondary structure and a net positive charge. Peptide antibiotics having this mode of action include the magainins, defensins, and the lantibiotics such as nisin. The activity of, this class of antibiotics is directed towards bacteria rather than mammalian cells because the positive charged residues of the antibiotic interact with negatively charged lipids which are found predominantly in bacterial rather than mammalian cell membranes.

In particular, the magainins are a class of amphiphilic α-helical peptides found in the skin of the African clawed frog (*Xenopus laevis*). Peptides of this class (which also include bombinin from amphibians [Gibson, B. W., Tang, D., Mandrell, R., Kelly, M. & Spindel, E. R. (1991) J. Biol. Chem. 266, 223103–23111], melittin from bee venom [Habermann, E. (1972) Science, 177, 314–322], and alamethicin from fungi [Latorre, R. & Alvarez, S. (1981) Physiol. Rev., 61, 77–150]) cause disruption of membrane potential at low concentrations, and membrane lysis via insertion at higher concentrations.

One group of antibiotics that has received widespread attention due to their clinical efficacy is the glycopeptide group of antibiotics. These agents consist of a rigid, cyclised heptapeptide backbone which may be substituted with a variety of amino and non-amino sugars. The amino sugar moieties of some members of this class contain N-acyl, N-alkyl, or N-aryl substitutions. Two antibiotics in this class are vancomycin and teicoplanin. Vancomycin is produced by *Streptococcus orientalis*, an actinomycete isolated from soil samples in Indonesia and India. The antibiotic was purified and its properties described shortly after its discovery (McCormick et al., 1956). Vancomycin is a complex tricyclic glycopeptide with a molecular mass of approximately 1500 Da. Its structure was determined by X-ray analysis (Sheldrick et al., 1978):

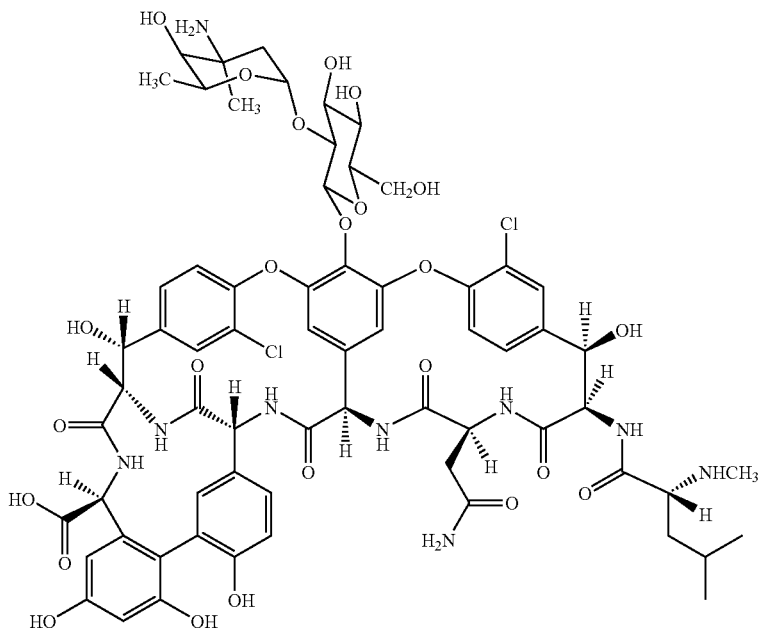

Vancomycin is active primarily against Gram-positive bacteria. Strains of bacteria are considered susceptible at a minimum inhibitory concentration of less than or equal to 4 µg/mL. *Strep. Pyogenes, Strep. Pneumoniae, Corynebacteraium* spp. are highly susceptible, as are most strains of *Enterococcus* spp. Most species of *Actinomyces* and *Clostridium* spp. are also sensitive to vancomycin, but at higher concentrations of antibiotic. Vancomycin is employed only to treat serious infections and is particularly useful in the management of infections due to methicillin-resistant staphylococci, including pneumonia, emphysema, endocarditis, osteomyelitis, and soft-tissue abscesses. The agent is also extremely useful in the treatment of staphylococcal infections in patients who are allergic to penicillins and cephalosporins.

Vancomycin inhibits the synthesis of the cell wall in sensitive bacteria by blocking the cross-linking of the sugar and peptidic components of peptidoglycans during the synthesis of the bacterial cell wall. Without sufficient cross-linking, the cell wall becomes mechanically fragile and the bacteria lyse when subjected to changes in osmotic pressure. Vancomycin binds with high affinity to the D-alanyl-D-alanine (D-Ala-D-Ala) terminus of the pentapeptide portion of the peptidoglycan precursor before cross-linking. The D-Ala-D-Ala dipeptide forms complementary hydrogen bonds with the peptide backbone of vancomycin. It is thought that the vancomycin-peptidoglycan complex physically blocks the action of the transpeptidase enzyme and thereby inhibits the formation of the peptide cross-bridges that strengthens the peptidoglycan. This activity also leads to the accumulation of peptidoglycan precursors in the bacterial cytoplasm.

Resistance to antibiotics is well documented and the resistant strains are a potential major threat to the wellbeing of mankind. Bacteria become resistant to an antimicrobial agent because either the drug fails to reach its target; the drug is inactivated, or because the target is altered. For example, some bacteria produce enzymes that reside in or within the cell surface and inactivate the drug, while others possess impermeable cell membranes that prevent influx of the drug.

Several types of resistance have been described for vancomycin, including the VanA-C types. The VanA phenotype is inducible by vancomycin and confers resistance to both teicoplanin and vancomycin. The VanA phenotype is mediated by the transposable element Tn1546 or closely related elements (Arthur et al., 1993). The transposon encodes a dehydrogenase (VanH) that reduces pyruvate to D-lactate (D-lac), and a ligase of broad substrate specificity (VanA) that catalyses the formation of an ester bond between D-Ala and D-Lac (Dukta-Malen et al., 1990; Bugg et al., 1991). The resulting D-Ala-D-Lac depsipeptide replaces the dipeptide D-Ala-D-Ala in the pathway of peptidoglycan synthesis. The substitution eliminates a hydrogen bond that is critical for antibiotic binding (Bugg et al., 1991). The VanB phenotype is also induced upon exposure to vancomycin; however, in contrast to the VanA phenotype, these microorganisms are not resistant to teicoplanin because teicoplanin does not induce the expression of the genes required for resistance in VanB bacteria (Arthur et al., 1996; Evers and Courvalin, 1996). Resistance to vancomycin by bacteria of the VanB phenotype occurs through a similar mechanism to VanA resistance, namely the substitution of the terminal D-Ala-A-Ala peptidoglycan precursor on the immature peptidoglycan by the D-Ala-D-Lac depsipeptide. One further vancomycin-resistant phenotype has been described (VanC) in enterococci belonging to the species *E. gallinarum, E. casseliflavus* and *E. flavescens*. These bacteria are intrinsically resistant to low levels of vancomycin and are susceptible to teicoplanin. Resistance results from the production of peptidoglycan precursors ending in D-Serine (Billot-Klein et al., 1994; Reynolds et al., 1994).

Substitution of D-Ala by D-Ser at the carboxy-terminus of the peptidoglycan precursor analogues lowers the affinity of the precursors for vancomycin with a relatively small change in the affinity for teicoplanin (Billot-Klein et al., 1994). The emergence and dissemination of high-level resistance to glycopeptides in enterococci in the past decade has resulted in clinical isolates resistant to all antibiotics of proven efficacy (Handwerger et al., 1992; Handwerger et al., 1993). The incidence of glycopeptide resistance among clinical isolates is increasing and enterococci have become important as nosocomial pathogens and as a reservoir of resistance genes (Murray 1990; Woodford et al., 1995). Nosocomial infection with multidrug resistant strains is potentially catastrophic and there is a need to identify novel anti-bacterial agents or methods of controlling bacterial infections.

Approaches that have been used to combat the emergence of antibiotic resistant strains include the modification of existing antibiotics to improve their potency against resistant organisms, or the discovery of new peptide antibiotics which kill their targets by permeabilizing the bacterial plasma membrane. Examples of the first approach have recently focussed on creating derivatives of glycopeptides such as vancomycin.

Functionalisation of the carboxyl terminal of vancomycin using the coupling agent 2-(1-hydroxybenzotriazol-1-yl)-1, 1,3,3-tetramethyluronium hexafluorophosphate (HBTU) has been successful in attaching short peptide sequences, both in solution and solid phases [Sundram, U. N. and Griffin, J. H. (1995) J. Org. Chem. 60 1102–1103]. The aminosugar and terminal amine moieties of vancomycin and related antibiotics. have also been derivatised. In a reductive alkylation approach, a series of compounds alkylated on the vancosamine sugar was created, some of which showed greatly improved activity vs vancomycin resistant bacterial strains [Cooper, R. D. G. et al. (1996) J. Antibiotics 49, 575–581; Rodriguez, M. J. et al. (1998) J. Antibiotics 51, 560–569].

WO-A-98/02454 describes polypeptide derivatives in which a soluble therapeutic polypeptide is modified with an entity of general structure:

-(L-[W])n-X (I)

in which each L is independently a flexible linker group, each W is independently a peptidic membrane-binding element, n is an integer greater than or equal to one, and X is a peptidic or non-peptidic membrane-binding or insertive element.

Structures of type (I) represent a combinatorial array of membrane-interactive elements whose attachment to soluble polypeptides was found to mediate binding of those polypeptides to the outer cell membrane of mammalian cells. This gave rise to therapeutic benefits, particularly in the case of regulators of complement activation acting as cytoprotectants and anti-inflammatory agents (e.g. Dong, J. et al, (1999) Mol. Immunol. 36 957–963).

SUMMARY OF THE INVENTION

The present inventors hypothesised that structures of type (I) would display even stronger binding to bacterial membranes which have a higher proportion of acidic phospholipids than do eukaryotic organisms, and have a higher proportion of membrane-associated biosynthetic proteins, and it has now been found that the anti-bacterial activity of compounds such as vancomycin and its derivatives can be increased when they are derivatised further with structures of type (I), and related structures.

Accordingly, a first aspect of the present invention provides a compound:

V-L-W- X (II) 

wherein
V is a glycopeptide moiety which inhibits peptidoglycan biosynthesis in bacteria;
L is a linking group;
W is a peptidic membrane-associating element; and
X is hydrogen or a membrane-insertive element.

Peptidoglycan Biosynthesis Inhibitor (V).

The first two stages of peptidoglycan occur inside the bacterial cell. Stage 1 involves the assembly of a N-acetyl-muramic acid based lipid with a linked pentapeptide, the peptide being:

L-Alanine-γ-D-Glutamate-Xaa-D-Alanine-D-Alanine (SEQ ID NO:39), where Xaa is usually m-D-amino pimelic acid but in some species (e.g. S. aureus) is L-lysine.

In the second stage, the lipid is extended by N-acetyl glucosamine. This lipid is subsequently transported across the cell membrane.

The third stage, which takes place on the exterior surface of the bacterial membrane, involves the polymerization of the lipid-linked GlcNAc-MurNAC-disaccharide by a trans-glycolase and the cross-linking of the peptide side chains by a transpeptidase.

The best known compound of the class of inhibitors of this biosynthesis pathway is vancomycin, which, as discussed above, is known to inhibit peptidoglycan biosynthesis by binding to the D-Ala-D-Ala dipeptide terminus of the pentapeptide of the bacterial cell wall peptidoglycan precursors, preventing their further processing into peptidoglycan.

Derivatives of vancomycin also act by inhibiting the biosynthesis of peptidoglycan. A series of compounds alkylated on the vancosamine sugar has been shown to have activity against vancomycin resistant bacteria, along with analogous compounds derivatized with a further sugar [Cooper, R. D. G. et al. (1996) J. Antibiotics 49, 575–581; Rodriguez, M. J. et al. (1998) J. Antibiotics 51, 560–569; Ge, M. et al. (1999) Science 284, 507–511].

In general, the moiety V is a glycopeptide moiety which inhibits peptidoglycan biosynthesis in bacteria. In general terms, those of skill in the art are familiar with glycopeptides of this class and may select suitable glycopeptides for use in the present invention. Such glycopeptides are typically of a molecular weight of from 1000 to 3000 Da, are capable of interaction with individual components of the bacterial peptidoglycan structure such as the Lys-D-Ala-D-Ala peptide, the Lys-D-Ala-D-Lactate depsipeptide, and components of the lipid GlcNAc-MurNAC-pentapeptide, and are active against vancomycin-susceptible reference strains (e.g. selected from any one of reference strains S. aureus NCTC (National Collection of Type Cultures) 6571, S. aureus ATCC 25923 (NCTC 12981), S. aureus ATCC 29213 (NCTC 12973), Streptococcus pneumoniae ATCC 49619 (NCTC 12977) and Enterococcus faecalis ATCC 29212 (NCTC 12697)) at a mic of less than or equal to 4 μg/ml. An accepted standard method for mic testing is the agar dilution method on IsoSensitest agar as recommended by the BSAC. It is published in The Journal of Antimicrobial Chemotherapy (1991), vol. 27, supplement D.

Particular vancomycin derivatives which are contemplated as the moiety V include compounds based on the glycopeptides disclosed in WO 96/30401 and WO 98/00153, and salts thereof, the disclosures of which are herein incorporated by reference.

Thus, preferred examples of the moiety V-L- include those of formula (III):

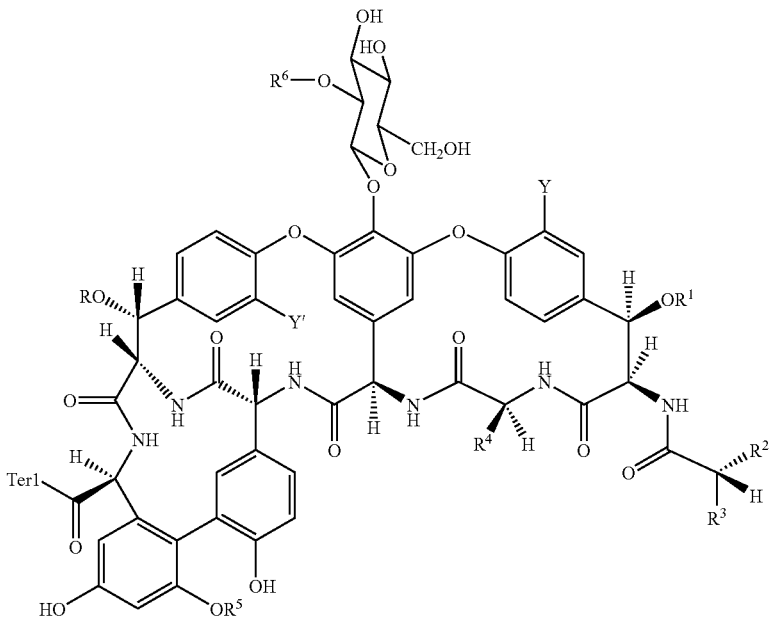

or salt thereof, in which:

Y and Y' are independently hydrogen or chloro;

R is hydrogen, 4-epi-vancosaminyl, actinosaminyl, ristosaminyl, or a group of the formula —Ra-L- wherein Ra is 4-epi-vancosaminyl, actinosaminyl, ristosaminyl and L (the linker of formula (II)) is attached to the amino group of Ra;

R1 is hydrogen, or mannose;

R2 is —NH2, —NHCH3, —N(CH3)2, —NHL-, or —N(CH3)L-

R3 is —CH2CH(CH3)2, [p-OH, m-Cl]phenyl, p-rhamnosephenyl, [p-rhamnose-galactose]phenyl, [p-galactose-galactose]phenyl, or [p-CH3O-rhamnose]phenyl;

R4 is —CH2-(CO)NH2, benzyl, [p-OH]phenyl, or [p-OH, m-Cl]phenyl;

R5 is hydrogen, or mannose,

R6 is hydrogen, 4-epi-vancosaminyl, vancosaminyl, actinosaminyl, ristosaminyl, or acosaminyl; or R6 is a group of the formula Rb-L- wherein Rb is 4-epi-vancosaminyl, vancosaminyl, actinosaminyl, ristosaminyl or acosaminyl and L is attached to the amino group of Rb; or R6 is a group Rb-R7 wherein R7 is an organic side chain moiety which is no more than 1000, preferably no more than 500 and preferably no more than 250 (such as no more than 150) Da;

Ter1 is hydroxy or -L-;

provided that the moiety includes at least one (for example two or three) group(s) -L-.

The precise nature of the organic side chain moiety is not a limiting feature of the present invention. Many thousands of such moieties are known as such in the art, including the numerous examples described in WO 96/30401 and WO 98/00153, the disclosures of which are incorporated herein by reference.

A subgroup of organic side chain moieties include those of the formula —CH2-R8, in which R8 is:

hydrogen,
alkyl of C1–C15,
alkenyl of C2–C15,
alkynyl of C2–C15,
haloalkyl of C1–C7,
acenaphthenyl,
2-fluorenyl,
9, 10-dihydro-2-phenanthrenyl,
R9,
alkyl of C1–C11-R9,
  alkenyl of C2–C7-R9,
  alkynyl of C2–C7-R9, or
  alkyl of C1–C7-O—R9 wherein R9 is a radical of the formula:

—R10-[linker(0 or 1)—R10](0 or 1)

wherein each R10 independently represents phenyl, cycloalkyl of C5–C6, naphthyl, or thienyl, each of which is unsubstituted or is optionally substituted with on or two substituents, each of which is independently alkyl of C1–C10, haloalkyl of C1–C2, haloalkoxy of C1–C2, alkoxy of C1–C10, halo, cyano, or nitro; and "linker" is:

-alkylene of C1–C3,
—O-alkylene of C1–C6,
-alkylene of C1–C6,
—O—,
—N(H or lower alkyl of C1–C3)-,
—S—,
—SO—,
—SO2-,
—NH—C(O)—,
—C(O)—NH—
—CH=CH—,
—CC—,
—N=N—,
—O—C(O)—, or
—C(O)—O—

"Halo" means fluoro, chloro, bromo or iodo; fluoro and chloro are preferred. Haloalkyl and haloalkoxy groups are preferably mono-substituted or di-substituted with the same halo group, although C1-3 haloalkyl groups may also be perfluoro groups.

Preferred examples of the group —CH2-R8 include:
(4-phenylbenzyl)
(4-(4-chlorophenyl)benzyl)
(4-(4-methylphenyl)benzyl)
(4-phenoxybenzyl)
((4-n-butylphenyl)benzyl)
(4-benzylbenzyl)

Compounds of the formula (III) include LY 264826, LY 191145 and LY 333328 as disclosed in Rodriguez, M. J. et al. (1998) J. Antibiotics 51, 560–569.

Particularly preferred examples of the moiety V include, but are not limited to, vancomycin, chloroeremomycin, teicoplanin A2-2, ristocetin A, eremomycin, balkimycin, actinodin A, complestanin, chloropeptin 1, kistamycin A and avoparcin.

Peptidic Membrane-associating Element (W).

This moiety (W) of the compound of formula II is a peptide which associates-with the bacterial membrane. While not wishing to be bound by any one particular theory, it is believed that the association of the element W with the bacterial membrane allows an increase in the local concentration of the glycopeptide antibiotic such that its reduced efficiency against resistant strains is alleviated by the increased concentration at the site of action.

The term "membrane associating" refers to two primary modes of action, binding to and/or insertion in the membrane. In the case of the former, the peptide is of a character which allows it to associate with elements on the surface of the bacterial membrane, such as negatively charged phospholipids. In the case of the latter, the element may be, or based upon, anti-bacterial peptides which have this property (for example derived from those found in nature).

Peptides may be prepared recombinantly or synthetically, e.g. by step-wise synthesis. Alternatively, the peptides may be recovered from cultures of cells which naturally produce the peptide, e.g. in the case of membrane associating peptides produced by bacteria.

Peptides produced by synthetic means will generally be composed of natural L-amino acids (i.e. those encoded by the genetic code, the so-called proteinogenic amino acids), although D-amino acids may also be used. In either case, side chain modifications may be performed, for example in order to enhance in vivo half life or improve stability. Side chain modifications include for example, modifications of amino groups by reductive alkylation by reaction with an aldehyde followed by reduction with NaBH4, amidination with methylacetimidate or acylation with acetic anhydride.

The guanidino groups of arginine residues may be modified by the formation of heterocyclic condensation products with reagents such as 2,3-butanedione or glyoxal. Sulphydryl groups may be modified by methods such as carboxymethylation, tryptophan residues may be modified by oxidation or alkylation of the indole ring and the imidazole ring of histidine residues may be modified by alkylation.

The carboxy terminus and any other carboxy side chains may be blocked in the form of an ester group, e.g. a C1-6alkyl ester or in the form of an amide.

The N-terminus may also be blocked.

The above examples of modifications to amino acids are not exhaustive. Those of skill in the art may modify amino acid side chains where desired using chemistry known per se in the art.

Peptides recovered from naturally occurring sources may contain non-proteinogenic amino acids, which are produced either by post translational modification of proteinogenic amino acids, or by biosynthesis.

The peptidic element may terminate with a cysteine or lysine residue or have such a residue within 1 or 2 amino acids from the C-terminal, in order to facilitate linking to the group V via the linker L. However, other amino acids are not excluded and may be used where the nature of the linking group is suitable for attachment to other moieties.

The peptide element W is generally of a size from 5 to 40 amino acids in length, preferably from 7 to 30 such as 8 to 30 amino acids.

It will be understood that unless indicated to the contrary, amino acid sequences are represented herein using standard notation and in the N- to C-terminal direction.

Membrane-binding Peptides.

Where the peptide is membrane binding, the element (W) may comprise a number of charged amino acid residues generally selected from arginine and lysine, particularly lysine, in order to facilitate interaction with the charged lipids found in bacterial membranes. Such peptides preferably include a least one sequence (Xaa)n, where n is from 1 to 12, preferably from 3 to 10, and each Xaa is independently lysine or arginine.

Thus, taking account of the overall preferences referred to above, W may be a peptide of from 5 to 40 amino acids comprising at least one sequence of from 1 to 12, more preferably from 2 to 10 such as from 3 to 10 contiguous residues selected from lysine and arginine.

Even more preferably, W may be a peptide of from 7, preferably 8 to 30 amino acids comprising at least one sequence of from 1 to 12, more preferably from 2, preferably 3 to 10 contiguous residues selected from lysine and arginine.

More preferably, W may be a peptide of from 7, preferably 8 to 30 amino acids comprising at least one sequence of from 1 to 12, more preferably from 2, preferably 3 to 10 contiguous lysine residues.

In all of the above embodiments, it is preferred that the peptide has an overall positive charge, e.g. from +1 to +10. Examples of such elements include:
DGPKKKKKKSPSKSSG (SEQ ID NO:4);
GSSKSPSKKKKKKPGD (SEQ ID NO:5);
SPSNETPKKKKKKRFSFKKSG (SEQ ID NO:6);
DGPKKKKKKSPSKSSK (SEQ ID NO:7); and
SKDGKKKKKKSKTK (SEQ ID NO:8).

Membrane-inserting Peptides.

Where the peptide is a membrane inserting peptide, such a peptide is one which itself has anti-bacterial activity, due to the action of the peptide disrupting the membrane, often by forming pores therein. By "antibacterial activity", it is meant that the conjugate of the peptide linked to vancomycin at the carboxy terminal of vancomycin, has an mic of no more than 0.064 mg/ml, preferably no more than 0.032 mg/ml, against the E. faecalis strains referred to above under the conditions referred to above.

Particular examples of such peptides include those derived from a natural source, such as from an animal. Certain peptides derived from a variety of sources, such as amphibian skin, are known to possess-membrane inserting properties, often accompanied by antibacterial properties.

A large number of groups of such peptides are known to possess such activity, including peptides reviewed in Jack & Jung, Chimia 52 (1988); 48–55, and McCafferty et al, Current Opinion in Chemical Biology (1999) 3; 672–680, the disclosures of which are incorporated herein by reference.

One group of peptides are α- and -defensins, produced by a wide variety of animal sources. The alpha defensins generally share substantial degrees of homology, contain a large number of Arg residues (but not Lys) and the disulfide-bond arrangement is uniformly conserved; disruption of the disulfide bonds results in loss of antimicrobial activity. The defensins are produced as prepro-peptides, and the leader- and pro-segments are probably involved in directing their transport to storage vesicles to await use. The -defensin TAP was isolated from bovine mucosa; -defensins are larger than the α-defensins and have a different disulfide arrangement. A large number of different defensin peptides and peptide families differing in their Arg/Lys content, number and arrangement of disulfide bonds and of differing overall length have been isolated, including HNP-1 and the tachyplesins which are 18-amino-acid antimicrobial peptides isolated from the horseshoe crab. The peptide TAP is part of a family of tachyplesins whose primary sequence varies slightly, but whose disulfide-bond arrangement and secondary structure remains conserved.

A great number of defensin-like peptides have now been described, having been isolated from a variety of sources including immune cells of mammals, mucosa, insect haemolymph, crustacea and plants and their seeds.

A further group of antimicrobial peptides have also been isolated from bacteria. Bacteriocins, or bacterial-derived antibacterial peptides, are produced by many different bacterial species. The structures vary considerably: some contain disulfide bonds, some contain free cysteine, some contain neither cysteine nor cystine and a fourth group consists of two peptides whose complementary presence is required for antimicrobial activity. However, regardless of their structural characteristics, they all act by forming hydrophilic pores in the cytoplasmic membrane of susceptible bacteria. These pores or channels depolarise the cytoplasmic membrane, disrupting energy transduction and ATP production.

One well-characterised bacteriocin is pediocin PA-1, produced by Pediococcus acidilactici PAC1.0. The bacteriocin contains no post-translational modifications, but does contain two essential disulfide bonds and a N-terminal sequence which is homologous with a number of other bacteriocins.

Lantibiotics are also bacteriocins and therefore they are ribosomally synthesised as precursor peptides. However, unlike the bacteriocins described above, the lantibiotics contain a large number of posttranslational modifications; the name lantibiotic is derived from their content in the thioether amino acids lanthionine and 3-methyllanthionine.

More than 25 lantibiotics have been characterised. Most lantibiotics are highly modified, many containing 50% (or more) non-proteinogenic α-amino acids.

In addition to the thioether amino acids, the lantibiotics contain a variety of other modified amino acids including 2,3-didehydroalanine and -butyrine, lysino-alanine, 2-aminovinyl-D-cysteine, hydroxy-aspartic acid, a number of N-terminal modifications and D-Ala. Not all lantibiotics contain each of these modified amino acids; in some cases, they are widespread, whilst in others they are specific to only one lantibiotic.

Particularly useful lantibiotics include type A lantibiotics which form pores in energised membrane bilayers, resulting in nonspecific, transient channels in the cytoplasmic membrane. Type A antibiotics include nisin and galligermin, the sequences of which are illustrated in Jack & Jung, 1998, ibid.

The following peptides are examples of those which may be of particular use in the present invention: magainin 1 and 2(Xenopus laevis) whose sequences are GIGKFLHSAGKFGKAFVGEIMK (SEQ ID NO:9) and GIGKFLHSAKKFGKAFVGEIMNS (SEQ ID NO:10) respectively, as well as those of Table 1 below.

TABLE 1

| Peptide | Structure | SEQ. ID NO: |
|---|---|---|
| Gramicidin | VGALAVVVWLWLWLW | 11 |
| Caerin 1.1 | GLLSVLGSVAKHVLPHVVPVIAEHL | 12 |
| Ranalexin | FLGGLIKIVPAMICAVTKKC | 13 |
| Maculatin 1.1 | GLFGVLAKVAAHVVPAIAEHF | 14 |
| GS14K4 | VKLKVYPLKVKLYP | 15 |
| Indolicidin | ILPWKWPWWPWRR | 16 |
| polymyxin B | cyclized isooctanoyl BTBB(BFdLBBT) | 17 |
| CP26 | KWKSFIKKLTSAAKKVVTTAKPLISS | 18 |
| CEMA | KWKLFKKIGIGAVLKVLTTGLPALTLTK | 19 |
| CP29 | KWKSFIKKLTTAVKKVLTTGLPALIS | 20 |

TABLE 1-continued

| Peptide | Structure | SEQ. ID NO: |
|---|---|---|
| CP11-NH2 | ILKKWPWWPWRRK-NH2 | 21 |
| CEME | KWKLFKKIGIGAVLKVLTTGLPALIS | 22 |
| bactenecin | Cyclized RL(CRIVVIRVC)R | 23 |
| linear Bac | RLCRIVVIRVCR | 24 |
| Bac2S | RLSRIVVIRVSR | 25 |
| gramicidin S | cyclic (PFdLOVPFdLOV) | 26 |
| Gram4112 | cyclic (PVKLKVdYdPLKVKLYd) | 27 |
| indolicidin | ILPWKWPWWPWRR-NH2 | 28 |
| Melittin | GIGAVLKVLTTGLPALISWIKRKRQQ | 29 |
| [D]-V5, 8I17K21 Melittin | GIGAdVLKdVLTTGLPALdISWIdKRKRQQ | 30 |
| Pexiganan | GIGKFLKKAKKFGKAFVKILKK | 31 |

"B" = diaminobenzoate,
"O" = ornithine,
"d" indicates the D enantiomer amino acid These and the other membrane inserting peptides referred to herein, or variants thereof such as those which have from 1 to 5 amino acid substitutions, insertions or deletions and which retain the activity defined above form a further group of the element W which may be used.

Examples of such variants include:
GIGKFLHSAKKFGKAFVAEIMNS (SEQ ID NO:32);
GIAKFLHSAKKFGKAFVAEIMNS (SEQ ID NO:33);
AAGKFLHSAKKFGKAFVGDIMNS (SEQ ID NO:34);
G-GKFLHSAKKFGKAFVGEIMNS (SEQ ID NO:35);
G-GKFIHSAKKFGKAFVGEIMNS (SEQ ID NO:36);
GIGKPIHSAKKFGKAFVGEIMNSK (SEQ ID NO:37); and
GIGAVLKVLTTGLPALISWIKRKRQQC (SEQ ID NO:38), where letters in bold show substitutions of, or additions to, the wild-type magainin or melittin sequences described above, and – indicates a deletion.

It is preferred that the peptides have an overall positive charge, e.g. from +1 to +10.

Linking Group L.

This linking group is all the atoms between the moiety V and the moiety W, and therefore the linking group must have at one end a moiety capable of linking to the peptidoglycan biosynthesis inhibitor (V), and at the other end a moiety capable of linking to the peptidic membrane-binding element (W).

It will be appreciated by those of skill in the art that compounds of the invention are generally synthesised by reacting a reactive derivative of W with a reactive derivative of V (with the group X either being attached to W before or after this step). Thus the structure -L- in the compounds of the invention will comprise atoms which were part of the reactive derivatives of both V and W.

Methods of providing reactive derivatives of glycopeptides and polypeptides are known per se in the art and those of skill in the art will be able to select from a range of methodologies in order to link V with W, resulting in a group L. Thus while the exact nature of the group L is not an essential feature of the invention, in one aspect this group is conveniently represented as:

$$-A-R-B-  \qquad (III)$$

where A is a group capable of linking to the peptidoglycan biosynthesis inhibitor (V), B is a group capable of linking to the peptidic membrane-binding element (W), and R is a bond or a group linking A and B.

Examples of linking groups of this type are the chemical bridging groups, for example as described in EP-A-109653, EP-A-152736, EP-A-155388 and EP-A-284413, the disclosures of which are incorporated herein by reference.

Linking to W

If W is to be joined through its N-terminus, or via an amine moiety on a side chain residue (e.g. the $\epsilon$-amino group of lysine), then B may be the radical of a moiety capable of reaction with an amine group. For example, the precursor to B may be a carboxylic acid (or derivative thereof), which when reacted with the N-terminus of the precursor to W, results in B being —C(=O)—, linked to W with an amide bond. In these embodiments, it is envisaged that the link is formed by reacting B=—R= with W=, where W= is the precursor to W, B= the precursor to B and R= a precursor of the remainder of the compound of formula II.

Alternatively, B may be a N-acetyl radical, —C(=O)—CH2-T-, where the carboxyl carbon is attached to the amine group of W, and T is selected from O, S, NH. Such a linkage can be formed by synthesising the N-haloacetyl derivative of W, followed by reaction with a appropriate precursor B'—R=, where B' is either OH, SH, or NH2.

If W is to be joined through its C-terminus, then B may be the radical of a moiety capable of reaction with a carboxylic acid group, which is usually a nucleophile. For example, the precursor to B may be an amine (or derivative thereof), which when reacted with the C-terminus of the precursor to W, results in B being —NH—, linked to W with an amide bond. In these embodiments, it is envisaged that the link is formed by reacting B=—R= with W=, where W= is the precursor to W, B= the precursor to B and R= a precursor of the remainder of the compound of formula II.

In the case where W terminates with a cysteine amino acid, then the linking group preferably terminates with sulphur, such that L joins to W by disulfide or thioether linkage. Thus, in formula (III), B is —S—. This linkage may be formed by activating the S on either the precursor to W or the precursor to B, for example, by forming a 2-pyridyl disulphide derivative which can react with a thio group to form the desired disulphide link.

Linking to V

Where V is vancomycin, the point of attachment of the linking group (L) is derived either from the amino terminus (2), from the amine of the vancosamine sugar (3) or, more preferably, from the carboxyl terminus (1).

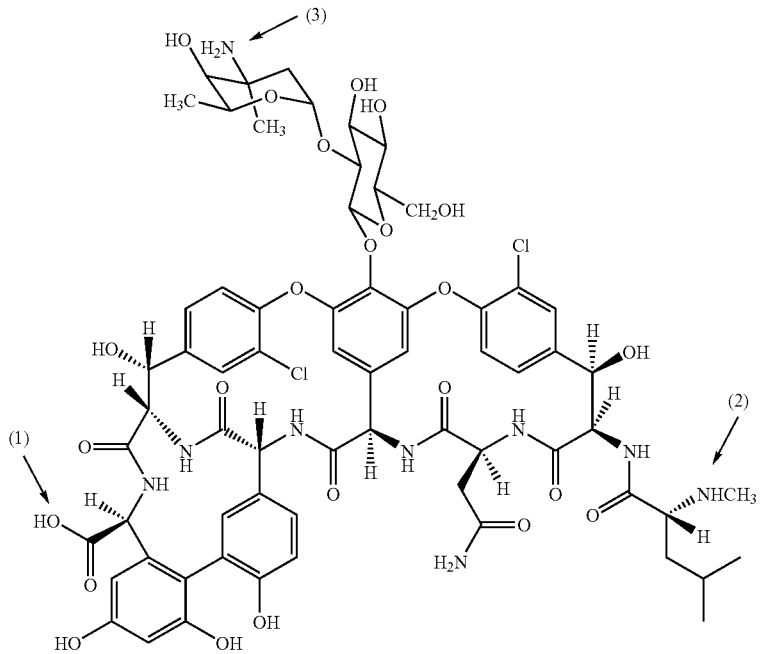

The means of derivatisation and linkage are as described above.

If V is a vancomycin derivative in which one of the above positions is already derivatised, then the point of attachment may be on one of the remaining available positions, or any suitable position on the derivatisation.

In the case where the group R is not a bond, but a group linking A and B, then it is preferably an alkylene chain containing from 3 to 12 carbon atoms, which chain may be interrupted by one or more hetero-atoms and/or aromatic rings, e.g. benzene or pyridine, and may contain one or more carbon-carbon double or triple bonds, and may be substituted with one or more functional groups.

Thus, R may include moieties which interact with water to maintain the water solubility of the linking group and suitable moieties include —CO—NH—, —CO—NMe—, —S—S—, —CH(OH)—, —SO2-, —CO2-, —(CH2CH2O) m- and —CH(COOH)—, where m is an integer of 2 or more.

Therefore examples of R include —(CH2)r-, —(CH2)p-S—S—(CH2)q- and —(CH2)p=—CH(OH)—CH(OH)—(CH2)q=-, in which r is an integer from 3 to 12, and p and q are independently integers whose total is from 3 to 12, and p= and q= are integers whose total is from 1 to 10.

Membrane-insertive Element X.

This element is optionally present on compounds of the invention. Where W is a membrane binding peptide, the presence of a membrane insertive element is preferred. Where W has these properties, the presence of a further insertive element is not excluded.

A range of elements with membrane insertive properties are known in the art. A preferred class which is contemplated by the present invention is a lipophilic chain based on carbon atoms. Many such chains are known in the art and the precise nature of the primary chemical structure is not essential to the invention, provided that the element is capable of having sufficient lipophilicity to partition into bacterial membranes when brought into contact with such membranes in an aqueous environment.

In general, the lipophilic chain based on carbon atoms is defined as:
  having from 6 to 30, preferably from 6 to 24 carbon atoms including those of any aromatic rings, if present;
  being straight or branched, and in the case of the latter containing one or more, for example two or three branch points;
  being saturated or unsaturated, in the case of the latter containing one or more, for example 2, 3 or 4, double or triple bonds;
  having 1, 2 or 3 heteroatoms (in addition to those, if present, in aromatic rings, if present, independently selected from S, O or N;
  optionally containing one or more, for example two or three, aromatic rings, which may be fused and each of which may contain from 1, 2 or 3 heteroatoms which, if present, are independently selected from N, O or S; and
  optionally having one or more (such as 1, 2 or 3) substituents selected from hydroxy, —SH, amino and halo (where halo is fluoro, chloro, bromo or iodo).

Preferably, the aromatic rings are six-membered, and may be selected from benzene and pyridine. If the rings are fused, then they may be selected from naphthalene, anthracene, quinolene and isoquinolene. Other examples of aromatic rings include thiophene and pyrrole.

In one embodiment, the element comprises an uninterrupted aliphatic carbon chain of at least six atoms, with preferably no more than 12, 16 or 20 carbon atoms. One group of such compounds have the structure —Ph—O—(CH2)t-H, where Ph is a benzene ring and t is from 6 to 12, 16, or 20.

In another, the element is a fatty acid, preferably those with 5 to 28 carbon atoms, optionally containing up to four, more preferably one or two carbon-carbon double bonds. Unsaturated radicals have the structure —C(O)—(CH2)t=-H, where t= is from 5 to 27, more preferably 9, 11, 13, 15, 17 or 19.

Another embodiment provides an element comprising the grouping —C(O)—Ph—Ph, where Ph is a phenyl group, which may be substituted, for example to provide an element —C(O)—Ph—Ph-p-Cl.

Another embodiment is an ether group within a fatty acid containing from 10 to 16 carbon atoms in total, which optionally contains one or two double bonds.

Another embodiment is a group of the formula Ph—CH(OH)—CH2—NH—C(Me2), where Ph is a phenylene ring substituted at the para position by a group RO—CH2-and the meta position by a group RO—, where each R is independently a C4-10 alkyl chain.

Administration of Drug

A second aspect of the present invention is a pharmaceutical composition comprising a compound of formula (II) and a pharmaceutically acceptable carrier.

The formulations optionally comprise other therapeutic ingredients, or diluents. The carrier or carriers must be "acceptable" in the sense of being compatible with the other ingredients of the formulation and not deleterious to the recipients thereof.

Formulations suitable for parenteral or intramuscular administration include aqueous and non-aqueous sterile injection solutions which may contain anti-oxidants, buffers, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets.

It should be understood that in addition to the ingredients particularly mentioned above, the formulations may include other agents conventional in the art having regard to the type of formulation in question. Of the possible formulations, sterile pyrogen-free aqueous and non-aqueous solutions are preferred.

Alternatively the composition may be formulated for topical application for example in the form of ointments, creams, lotions, eye ointments, eye drops, ear drops, mouthwash, impregnated dressings and sutures, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections.

Many orthopaedic surgeons consider that patients with prosthetic joints should be considered for antibiotic prophylaxis before dental treatment that could produce a bacteraemia. Late deep infection is a serious complication sometimes leading to loss of the prosthetic joint and is accompanied by significant morbidity and mortality. It is therefore possible to extend the use of the peptide or peptide/drug conjugate as a replacement for prophylactic antibiotics in this situation.

Bacterial infections cause one of the major complications associated with the clinical use of implanted materials and in-dwelling devices. In particular, staphylococci have frequently been implicated in medical device-related infections (Dankert et al 1986, CRC Rev Biocompatability 2, 219–301). Once established, the infection is virtually impossible to treat resulting in implant failure. Attempts to combat staphylococcal adhesion to implants have involved modification of the surface of the prosthetic material to discourage adhesion of proteins; e.g. coating with a "non-stick" material such as PTFE, or bonding antibiotics to the surface (Kamal et al., 1991, J. Amer. Med. Assoc. 265, 2364–2368). In addition, there have also been proposals to use non-steroidal anti-inflammatory drugs to prevent adhesion of staphylococci to medical polymers (Farber and Wolff 1992, J. Infect. Dis. 166: 861–865).

For administration to human patients, it is expected that the daily dosage level of the active agent will be from 0.01 to 50 mg/kg, typically around 1 mg/kg. The physician in any event will determine the actual dosage most suitable for an individual patient, and will vary with the age, weight, and response of the particular patient. The above dosages are exemplary of the average case. There can, of course, be individual instances where higher or lower dosage ranges are merited, and such are within the scope of this invention.

In addition to the therapy described above, the compositions of this invention may be used generally as a wound treatment agent to prevent adhesion of bacteria to matrix proteins, especially fibronectin, exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 0.1 g/ml to 10 mg/ml for bathing of wounds or indwelling devices.

Compositions of the invention may be used for, but are not restricted to, the treatment of bacterial infections caused by the following organisms: *Mycobacterium* sp.; *Enterococcus* sp.; *Escherichia* sp.; *Staphylococcus* sp.; *Streptococcus* sp.; *Vibrio* sp.; *Neisseria* sp.; *Borrelia* sp.; *Klebsiella* sp.; *Hemophilus* sp.; *Clostridium* sp.; *Pseudomonas* sp.; *Actinomyces* sp.; *Pneumococcus* sp.; *Salmonella* sp.

In a further aspects of the present invention, compounds of formula (II) may be used as a pharmaceutical or in methods of treatment of the animal or human body, and in particular for treatment of bacterial infections caused by the above listed organisms. Compounds of formula (II) may also be used in the manufacture of a medicament for the treatment of bacterial infections, particularly those caused by the above listed organisms.

EXAMPLES

Embodiments of the present invention will now be described in detail by way of example.

Methods

Haemolysis Assay

Lysis of sensitised sheep erythrocytes was measured using a standard haemolytic assay using a v-bottom microtitre plate format as follows:

50 microlitres of a range of concentrations of compound diluted in Hepes buffer were mixed with 100 microlitres of sensitised sheep erythrocytes and then incubated for 1 hour at 37° C. Samples were spun at 1600 rpm at ambient temperature for 3 minutes before transferring 150 microlitres of supernatant to a flat bottom microtitre plate and determining the absorption at 405 or 410 nm. Maximum lysis (Amax) was determined by incubating serum with erythrbcytes in the presence of human serum diluted 1:400 (final concentration in assay mixture) in 0.1 M Hepes/0.15 M NaCl/0.1% gelatin pH 7.4. Background lysis (Ao) was determined by incubating erythrocytes in the absence of any serum or compound, using PBS as a control. Lysis was expressed as a fraction of 100% total cell lysis such that LC50 represents the concentration of compound required to give 50% lysis. Antibiotics with low lytic activity in erythrocytes compared to their antibacterial activity are advantageous.

Antimicrobial Activity Assay

Compounds were tested for antimicrobial activity against a variety of bacterial strains that included one or more of the following microorganisms: *Escherichia coli* strain TG1, *Bacillus subtilis* strain 168S, *Staphylococcus aureus* H, *Enterococcus faecium* STR 207 (Van A resistant phenotype), *Enrterococcus faecium* STR211 (Vancomycin sensitive phenotype), and *Enterococcus faecalis* V 583 (Van B resistant phenotype). For the testing of compounds for antimicrobial activity against *E. coli* and *B. subtilis* cultures of each bacterial strain were diluted in 2.5 mL of fresh LB broth to approximately 5×106 cells/mL for assay. Compounds to be tested were diluted in water and added to the bacterial cultures to give final concentrations between 200 µg/mL and 0.5 ng/mL. The cultures were grown with shaking for up to 16 h at 37° C. for *E. coli* cultures and 30° C. for *B. subtilis* cultures. Antibacterial activity was determined from inspection of the turbidity of the different cultures and from determination of the optical density of the cultures at a wavelength of 600 nm. For the testing of compounds for antimicrobial activity against *E. Faecium* STR 207, *E. faecium* 211, *E. faecalis* V 583, and *S. aureus* H, a different procedure was used. These microorganisms were cultured in brain heart/0.5% yeast extract (BHY) broth and incubated overnight at 37° C. A sample of each culture was then diluted 40-fold in fresh BHY broth and incubated at 37° C. for 1 h. The resultant mid-log phase cultures were diluted to 106 cfu/mL, then added to wells of 96-well polypropylene plates. Vancomycin,was serially diluted 2-fold across the culture containing wells from 128 to 0.0156 µg/mL. Test compounds were then serially diluted in a similar manner across the culture containing wells from 512 µg/mL to 0.03 µg/mL. The 96-well plates were covered and incubated at 37° C. overnight. Minimum inhibitory concentrations were determined by inspection of turbidity after incubation.

Example 1

Synthesis and Characterisation of APT542

(MSWP-1, Example 2 of WO/9802454). The peptide: Gly-Ser-Ser-Lys-Ser-Pro-Ser-Lys-Lys-Lys-Lys-Lys-Pro-Gly-Asp-Cys-NH2 (SEQ ID NO:1) was prepared using solid phase synthesis via the general Fmoc/tBu strategy developed by Sheppard and Atherton (E. Atherton and R. C. Sheppard, Solid Phase Synthesis, IRL Press, Oxford, 1989). Kieselguhr-supported polydimethylacrylamide resin (Macrosorb 100) was used as the solid support and was derivatised with ethylene diamine.

Coupling reactions were carried out using N-α-Fmoc protected reagents pre-activated with N,N'-diisopropylcarbodiimide/N-hydroxybenzotriazole (in 4-fold molar excess) with bromophenol blue monitoring. Fmoc Cleavages used 20% piperidine in DMF. Reactions to assemble the peptide chain were carried out by repeated cycles of coupling and deprotection including the attachment of the modified Rink linkage reagent (p-[(R,S)-α-[1-(9H-fluoreny-9-yl-methoxyformamido]-2,4 dimethoxybenzyl]-phenoxyacetic acid) designed to yield a C-terminal amide on final cleavage. The side chain functionalities of the individual amino-acids were protected as follows: Ser (tButyl), Lys (Boc), Asp (O-tButyl), Cys (Trityl).

On completion of the peptide assembly and with the peptide still attached to the resin, a myristoyl group was attached to the amino group of the N terminal glycine by direct coupling of myristic acid using the same activation procedure. This modified peptide was then cleaved from the resin and the side-chain protecting groups removed at the same time by treatment with trifluoracetic acid containing 2.5% water and 2.5% triisopropyl silane.

The crude product was treated with 2,2'-dithiopyridine in 0.01 M ammonium acetate solution at pH 8-9 for approx. 2 h, then acidified with acetic acid and purified by preparative high performance liquid chromatography (HPLC) with 0.1% trifluoracetic acid (TFA)/water and 0.1% TFA/acetonitrile as gradient components. After lyophilisation, the peptide was a white amorphous powder, soluble to at least 10 mg/ml in dimethylsulphoxide. Fast atom bombardment mass spectrometry gave main peaks at m/e 2107.8, 2129.7 and 2145.8, corresponding to the monoprotonated, monosodiated and monopotassiated molecular ions of the peptide. The 2-thiopyridyl content of the peptide was measured by dissolving it to around 0.03 mM to 0.2 mM in 0.1 M Sodium Borate pH 8.0 and reducing by addition of dithiothreitol to 5 mM. The change in optical density at 343 nm was used to calculate the amount of pyridine 2-thione released using an extinction coefficient at this wavelength of 8080 cm−1 M−1. This indicated that the peptide content was approximately 60% of the dry weight.

The final produce thus has the structure:N-(Myristoyl)-Gly-Ser-Ser-Lys-Ser-Pro-Ser-Lys-Lys-Lys-Lys-Lys-Pro-Gly-Asp-(S-2-thiopyridyl)-Cys-NH2 APT542 was tested for antimicrobial activity against *E. coli* strain TG1 and *B. subtilis* 168S as described in Methods. The minimum inhibitory concentration of APT542 to prevent the growth of *E. coli* strain TG1 was 0.022 mg/mL after 6 h and 0.067 mg/mL after 16 h. The minimum inhibitory concentration of APT542 to prevent the growth of *B. subtilis strain* 168S was 0.003 mg/mL after 6 h and 0.022 mg/mL after 24 h growth. The antibacterial activity of APT542 was also determined against *E. faecium* STR 207, *E. faecalis* V 583, *E. faecium* STR 211 and *S. aureus* H, as described in Methods. The minimum inhibitory concentration of APT542 was 0.064 mg/mL, 0.256 mg/mL, 0.032 mg/mL, and 0.064 mg/mL for each microorganism respectively.

Example 2

Synthesis and Characterisation of APT540

APT540 is a dimer of APT542, linked via a cysteine bridge through the C-terminal cys residues.

APT542 (Example 1; Example 2 in WO 98/02454; 54 mg) was dissolved in 0.1 M Tris pH 8.5 (2.68 mL) and treated with 0.35 molar equivalents of tris-2-carboxyethyl phosphine (TCEP) dissolved in water. The reaction was allowed to proceed for 30 minutes at room temperature and analysed by HPLC using a C18 reverse phase column with a gradient of 35%–90% acetonitrile in 0.1% trifluoroacetic acid. Reaction products were monitored at wavelengths of 210 nm and 310 nm. APT540 was identified as a peak eluting from the column at approximately 10.5 minutes after injection. The material corresponding to the APT540 compound was collected and lyophilised. Mass spectrometry of this sample using a PerSeptive Biosystems instrument identified a major peak of 3998 daltons which corresponds to the theoretical molecular weight of APT540. APT540 was tested for antimicrobial activity against *E. coli* strain TG1 and *B. subtilis* 168S as described in Methods. The minimum inhibitory concentration of APT540 to prevent the growth of *E. coli* strain TG1 was 0.067 mg/mL after 6 h and 0.2 mg/mL after 16 h. The minimum inhibitory concentration of APT540 to prevent the growth of *B. subtilis* strain 168S was 0.007 mg/mL after 6 h and 24 h growth.

Example 3

Synthesis and Characterization of APT541

APT541 is an N-myristoyl derivative of SEQ ID NO:1, which is further derivatised at its C-terminus by the addition of a cysteine residue on the side chain of the C-terminal cysteine.

APT542 (Example 1; 10 mM in 100 mM Tris pH 8.5; 1.3 mL) was mixed with 100 mM cysteine (0.1 mL) and stirred over 2 h. The reaction mixture was purified by preparative HPLC using a gradient of 0–100 % acetonitrile in 0.1% trifluoroacetic acid over 10 minutes. The product eluted at approximately 10.0 minutes, and was collected. Evaporation of volatiles and lyophilisation afforded APT541 as a white solid. MALDI TOF Mass Spec. $C_{92}H_{168}N_{26}O_{26}S_2$ requires: 2117.2 Da. Found: 2117.3 Da. When purified APT541 was treated with excess 1 mM DTT, no increase in absorbance at 343 nm was observed which indicated that all thiopyridyl groups had been replaced.

The antibacterial activity of APT541 was also determined against *E. faecium* STR 207, *E. faecalis* V 583, *E. faecium* STR 211, and *S. aureus* H, as described in Methods. The minimum inhibitory concentration of APT541 was 0.128 mg/mL, 0.256 mg/mL, 0.064 mg/mL, and 0.064 mg/mL for each microorganism respectively.

Example 4

Synthesis and Characterisation of APT537

The peptide of SEQ ID NO:2 was synthesised using the same overall methodology as used in Example 1. The most significant change was the replacement of three of the lysine residues by aspartate residues. The peptide was linked at its N-terminus to a myristoyl group, and an S-linked 2-thiopyridyl group introduced as in example 1.

Example 5

Synthesis and Characterisation of APT539

APT539 was synthesised using the same overall methodology as used in Example 1, using the peptide of SEQ ID NO:1. The most significant difference was the replacement of myristic acid with lauric acid.

Example 6

Synthesis and Characterisation of APT538

APT538 was synthesised using the same overall methodology as used in Example 1, using the peptide of SEQ ID NO:1. The most significant difference was the replacement of myristic acid with decanoic acid.

Example 7

Synthesis and Characterisation of APT171

APT171 was synthesised using the same overall methodology as used in Example 1, using the peptide of SEQ ID NO:1. The most significant difference was the replacement of myristic acid with octanoic acid.

Example 8

Synthesis and Characterisation of APT170

APT170 was synthesised using the same overall methodology as used in Example 1, using the peptide of SEQ ID NO:1. The most significant difference was the replacement of myristic acid with butanoic acid.

Example 9

Synthesis and Characterisation of APT2197

APT2197 was synthesised using the same overall methodology as used in Example 1, using the peptide of SEQ ID NO:1. The most significant difference was the replacement of myristic acid by palmitic acid.

Example 10

Synthesis and Characterisation of APT2198

APT2198 was synthesised using the same overall methodology as used in Example 1, using the peptide of SEQ ID NO:1. The most significant difference was the replacement of myristic acid with octadecanoic acid.

Example 11

Synthesis and Characterisation of APT2199

APT2199 was synthesised using the same overall methodology as used in Example 1, using the peptide of SEQ ID NO:1. The most significant difference was the replacement of myristic acid with eicosanoic acid.

Example 12

Synthesis and Characterisation of APT2200

APT2200 was synthesised using the same overall methodology as used in Example 1, using the peptide of SEQ ID NO:1. The most significant difference was the replacement of myristic acid with 4-biphenyl-carboxylic acid.

Example 13

Synthesis and Characterisation of APT2235

APT2235 was synthesised using the same overall methodology as used in Example 1, using a peptide of SEQ ID NO:3, and omitting attachment of a group at the N-terminus, but retaining the 2-thiopyridyl derivatisation at the C-terminus. The LC50 was determined to be 1.2 µM.

Example 14

Synthesis of APT2036 N-(Myristoyl)-Gly-Ser-Ser-Lys-Ser-Pro-Ser-Lys-Lys-Lys-Lys-Lys-Lys-Pro-Gly-Asp-(S-thioethyl-2-vancomycin carboxamide)-Cys-NH2 (Structure 3)

APT2036, was synthesised chemically in three steps from vancomycin. Vancomycin hydrochloride (100 mg, 0.0673 mmol) was dissolved in dry dimethylformamide (1 mL) and dry methyl sulfoxide (1 mL). 2-Aminoethyl-2'-pyridyldisulfide dihydrochloride (34.8 mg, 0.1346 mmol) was added and the mixture cooled to 0° C. under an atmosphere of dry nitrogen. 2-(1-Hydroxybenzotriazol-1-yl)-1,1,3,3-tetramethyluronium hexafluorophosphate (0.234 mL of a 0.45 M solution in dry dimethylformamide, 0.1 mmol) and hydroxybenzotriazole (1 mg, cat.) were added, the mixture allowed to warm to ambient temperature, and stirred for 6 h. The reaction was characterised by the disappearance of vancomycin and the appearance of the product (APT2033—Structure 1 as shown in the table below) by HPLC. The product was purified using preparative HPLC using a gradient of 10–90% buffer B in buffer A over 20 minutes (buffer A: 0.1% trifluoroacetic acid; buffer B: 90% acetonitrile, 0.1% trifluoroacetic acid), and a Jupiter C18, 250×10 mm, 300 Å column running at 5 mL/min. The volatile components were removed in vacuo and the aqueous solution lyophilised to afford APT2033 as a white hydrochloride salt. Retention time 8.4 min; MALDI TOF Mass Spec. $C_{73}H_{86}Cl_3N_{11}O_{22}S_2$ requires: 1640.0 Da. Found. 1638.5 Da. The antibacterial activity of APT2033 was determined against E. faecium STR 207, E. faecalis V 583, E. faecium STR 211, and S. aureus H, as described in Methods. The minimum inhibitory concentration of APT2033 was 0.256 mg/mL, 0.032 mg/mL, 0.002 mg/mL, and 0.004 mg/mL for each microorganism respectively. LC50 No lysis observed at highest concentration of 166 µM.

APT2033 (9.9 mg, 0.00617 mmol) was dissolved in water (1 mL) and tris-2-carboxyethyl phosphine (1.9 mL of a 10 mM solution in 50 mM HEPES pH 4.5) added with stirring. The mixture was stirred over 30 minutes and the product (APT2035—Structure 2) purified and isolated as for APT 2033. Retention time 7.0 min; MALDI TOF Mass Spec. $C_{68}H_{83}Cl_3N_{10}O_{22}S$ requires: 1530.9 Da. Found. 1529.1 Da. The antibacterial activity of APT2035 was also determined against E. faecium STR 207, E. faecalis V 583, E. faecium STR 211, and S. aureus H, as described in Methods. The minimum inhibitory concentration of APT2035 was 0.128 mg/mL, 0.016 mg/mL, 0.002 mg/mL, and 0.008 mg/mL for each microorganism respectively. LC50 No lysis observed at highest concentration of 166 µM.

APT2035 (1.62 mg, 0.00108 mmol) was dissolved in water (0.2 mL) and MSWP1 (0.04 mL of a 21.6 mM solution in dry methyl sulfoxide, 0.87 µmol) added. The mixture was stirred over 2 h before the product (APT2036—Structure 3 as shown in the table below) was purified by preparative HPLC (10–90 % buffer B over 20 minutes) and isolated as its hydrochloride salt as for APT2033. Retention time 13.5 min; MALDI TOF Mass Spec. $C_{157}H_{244}Cl_3N_{35}O_{46}S_2$ requires: 3528.4 Da. Found. 3528.1 Da. The antibacterial activity of APT2036 was also determined against E. faecium STR 207, E. faecalis V 583, E. faecium STR 211, and S. aureus H, as described in Methods. The minimum inhibitory concentration of APT2036 was 0.008 mg/ml, 0.008 mg/ml, 0.008 mg/ml, and 0.004 mg/ml for each microorganism respectively. LC50 71 uM.

Example 15

Synthesis of APT2037 N-(Lauroyl)-Gly-Ser-Ser-Lys-Ser-Pro-Ser-Lys-Lys-Lys-Lys-Lys-Lys-Pro-Gly-Asp-(S-thioethyl-2-vancomycin carboxamide)-Cys-NH2 (Structure 4)

APT2037 was synthesised using the same overall methodology as used in Example 9. The most significant difference was the replacement of APT542 with APT539, to give the structure shown. Retention time 11.9 min; The antibacterial activity of APT2037 was also determined against E. faecium STR 207, E. faecalis V 583, E. faecium STR 211, and S. aureus H, as described in Methods. The minimum inhibitory concentration of APT2037 for each microorganism was 0.016 mg/ml, 0.016 mg/ml, 0.004 mg/ml, and 0.008 mg/ml respectively. LC30 71 uM.

Example 16

Synthesis of APT2038 N-(Decanoyl)-Gly-Ser-Ser-Lys-Ser-Pro-Ser-Lys-Lys-Lys-Lys-Lys-Lys-Pro-Gly-Asp-(S-thioethyl-2-vancomycin carboxamide)-Cys-NH2 (Structure 5)

APT2038 was synthesised using the same overall methodology as used in Example 9. The most significant difference was the replacement of APT542 with APT538, to give the structure shown. Retention time 10.7 min; The antibacterial activity of APT2038 was also determined against E. faecium STR 207, E. faecalis V 583, E. faecium STR 211, and *S. aureus* H, as described in Methods. The minimum inhibitory concentration of APT2038 for each microorganism was 0.064 mg/ml, 0.064 mg/ml, 0.002 mg/ml, and 0.008 mg/ml respectively. LC10 71 uM.

Example 17

Synthesis of APT2039 N-(Octanoyl)-Gly-Ser-Ser-Lys-Ser-Pro-Ser-Lys-Lys-Lys-Lys-Lys-Lys-Pro-Gly-Asp-(S-thioethyl-2-vancomycin carboxamide)-Cys-NH2 (Structure 6)

APT2039 was synthesised using the same overall methodology as used in Example 9. The most significant difference was the replacement of APT542 with APT171, to give the structure shown. Retention time 9.0 min; The antibacterial activity of APT2039 was also determined against *E. faecium* STR 207, *E. faecalis* V 583, *E. faecium* STR 211, and *S. aureus* H, as described in Methods. The minimum inhibitory concentration of APT2039 for each microorganism was 0.128 mg/ml, 0.128 mg/ml, 0.002 mg/ml, and 0.0016 mg/ml respectively. LC30 no lysis at 71 uM.

Example 18

Synthesis of APT2040 N-(n-Butyl)-Gly-Ser-Ser-Lys-Ser-Pro-Ser-Lys-Lys-Lys-Lys-Lys-Lys-Pro-Gly-Asp-(S-thioethyl-2-vancomycin carboxamide)-Cys-NH2 (Structure 7)

APT2040 is synthesised using the same overall methodology as used in Example 9. The most significant difference is the replacement of APT542 with APT170, to give the structure shown.

Example 19

Synthesis of APT2041 N-(Myristoyl)-Gly-Ser-Ser-Lys-Ser-Pro-Ser-Lys-Asp-Lys-Asp-Lys-Asp-Pro-Gly-Asp-(S-thioethyl-2-vancomycin carboxamide)-Cys-NH2 (Structure 8)

APT2041 was synthesised using the same overall methodology as used in Example 9. The most significant difference is the replacement of APT542 with APT537, to give the structure shown. Retention time 14.1 min; The antibacterial activity of APT2041 was also determined against *E. faecium* Str 207, *E. faecalis* V 583, *E. faecium* STR 211, and *S. aureus* H, as described in Methods. The minimum inhibitory concentration of APT2041 Was 0.016 mg/ml, 0.016 mg/ml, 0.004 mg/ml, and 0.008 mg/ml for each microorganism respectively. LC50 4.5 uM.

Example 20

Synthesis of APT2208 N-(Palmitoyl)-Gly-Ser-Ser-Lys-Ser-Pro-Ser-Lys-Lys-Lys-Lys-Lys-Lys-Pro-Gly-Asp-(S-thioethyl-2-vancomycin carboxamide)-Cys-NH2 (Structure 9)

APT2208 was synthesised using the same overall methodology as used in Example 9. The most significant difference is the replacement of APT542 with APT2197, to give the structure shown. Retention time 15.2 min; The antibacterial activity of APT2208 was also determined against *E. faecium* STR 207, *E. faecalis* V 583, *E. faecium* STR,211,.. and *S. aureus* H, as described in Methods. The minimum inhibitory concentration of APT2208 was 0.008 mg/ml, 0.016 mg/ml, 0.002 mg/ml, and 0.004 mg/ml for each microorganism respectively.

Example 21

Synthesis of APT2209 N-(Octadecanoyl)-Gly-Ser-Ser-Lys-Ser-Pro-Ser-Lys-Lys-Lys-Lys-Lys-Lys-Pro-Gly-Asp-(S-thioethyl-2-vancomycin carboxamide)-Cys-NH2 (Structure 10)

APT2209 was synthesised using the same overall methodology as used in Example 9. The most significant difference is the replacement of APT542 with APT2198, to give the structure shown. Retention time 16.7 min; The antibacterial activity of APT2209 was also determined against *E. faecium* STR 207, *E. faecalis* V 583, *E. faecium* STR 211, and *S. aureus* H, as described in Methods. The minimum inhibitory concentration of APT2209 was 0.032 mg/ml, 0.064 mg/ml, 0.016 mg/ml, and 0.032 mg/ml for each microorganism respectively.

Example 22

Synthesis of APT2210 N-(Eicosanoyl)-Gly-Ser-Ser-Lys-Ser-Pro-Ser-Lys-Lys-Lys-Lys-Lys-Lys-Pro-Gly-Asp-(S-thioethyl-2-vancomycin carboxamide)-Cys-NH2 (Structure 11)

APT2210 was synthesised using the same overall methodology as used in Example 9. The most significant difference is the replacement of APT542 with APT2199, to give the structure shown. Retention time 18.45 min; The antibacterial activity of APT2210 was also determined against *E. faecium* STR 207, *E. faecalis* V 583, *E. faecium* STR 211, and *S. aureus* H, as described in Methods. The minimum inhibitory concentration of APT2210 was 0.128 mg/ml, 0.128 mg/ml, 0.032 mg/ml, and >0.128 mg/ml for each microorganism respectively.

Example 23

Synthesis of APT2211 N-(4-Biphenylcarboxyl)-Gly-Ser-Ser-Lys-Ser-Pro-Ser-Lys-Lys-Lys-Lys-Lys-Lys-Pro-Gly-Asp-(S-thioethyl-2-vancomycin carboxamide)-Cys-NH2 (Structure 12)

APT2211 was synthesised using the same overall methodology as used in Example 9. The most significant difference is the replacement of APT542 with APT2200, to give the structure shown. Retention time 9.3 min; The antibacterial activity of APT2211 was also determined against *E. faecium* STR 207, *E. faecalis* V 583, *E. faecium* STR 211, and *S. aureus* H, as described in Methods. The minimum inhibitory concentration of APT2211 was 0.008 mg/ml, 0.032 mg/ml, <0.03 mg/ml, and 0.00025 mg/ml for each microorganism respectively. LC50 no lysis at 166 M.

Example 24

Synthesis of APT2122 N-(Myristoyl)-Gly-Ser-Ser-Lys-Ser-Pro-Ser-Lys-Lys-Lys-Lys-Lys-Lys-Pro-Gly-Asp-(S-2-thioethyl-succinyl-vancomycin vancosaminide)-Cys-NH2 (Structure 15)

APT2122 was synthesised chemically in three steps from vancomycin. Vancomycin hydrochloride (100 mg, 0.0673 mmol) was dissolved in dry dimethylformamide (4 mL) and DIEA (12.9 µL, 0.0742 mmol) added. 2-Aminoethyl-2'-pyridyldisulfide dihydrochloride (0.500 g, 1.93 mmol) was dissolved in water (20 mL) and dichloromethane (20 mL) added. 1 M NaOH was added dropwise to take the pH to 12, the organic layer extracted, dried over anhydrous magnesium sulphate, and filtered. Succinic anhydride (193 mg, 1.93 mmol) and DIEA (0.5 mL) were added and the mixture stirred at ambient temperature over 1 h. 1.04 mL Of this mixture was evaporated and dissolved in DMF (300 µL). PyBOP (57.8 mg, 111.1 µmol) And DIEA (19.3 µL, 111.1 µmol) were added, the mixture stirred over 15 mins, then added to the solution of vancomycin. After 6 h the reaction was characterised by the disappearance of vancomycin and the appearance of the product (APT2116-Structure 13) by HPLC. The product was purified as for APT2036 to afford APT2116 (structure 9) as a white hydrochloride salt. Retention time 8.2 min; MALDI TOF Mass Spec. $C_{77}H_{90}Cl_3N_{11}O_{25}S_2$ requires: 1740.1 Da. Found. 1739.4 Da. The antibacterial activity of APT2116 was determined against *E. faecium* STR 207, *E. faecalis* V 583, *E. faecium* STR 211, and *S. aureus* H, as described in Methods. The minimum inhibitory concentration of APT2116 was 0.512 mg/mL, 0.256 mg/mL, 0.032 mg/mL, and >0.512 mg/mL for each microorganism respectively.

APT2116 (8.3 mg, 0.00477 mmol) was dissolved in water (0.5 mL) and tris-2-carboxyethyl phosphine (1.3 mL of a 10 mM solution in 50 mM HEPES pH 4.5) added with stirring. The mixture was stirred over 30 minutes and the product (APT2117-Structure 14) purified and isolated as for APT 2116. Retention time 7.1 min; MALDI TOF Mass Spec. $C_{72}H_{87}C_{13}N_{10}O_{25}S$ requires: 1630.9 Da. Found. 1632.0 Da. The antibacterial activity of APT2117 was also determined against *E. faecium* STR 207, *E. faecalis* V 583, *E. faecium* STR 211, and *S. aureus* H, as described in Methods. The minimum inhibitory concentration of APT2117 was >512 mg/mL, 512 mg/mL, 0.008 mg/mL, and 0.008 mg/mL for each microorganism respectively.

APT2117 (1.41 mg, 0.864 mmol) was dissolved in water (0.20 mL) and MSWP1 (0.022 mL of a 21.6 mM solution in dry methyl sulfoxide, 0.475 µmol) added. The mixture was stirred over 2 h before the product (APT2122—Structure 15) was isolated as for APT2116. Retention time 13.8 min; MALDI TOF Mass Spec. $C_{157}H_{243}Cl_2N_{35}O_{46}S_2$ requires: 3628.4 Da. Found. 3638.4 Da. The antibacterial activity of APT2122 was also determined against *E. faecium* STR 207, *E. faecalis* V 583, *E. faecium* STR 211, and *S. aureus* H, as described in Methods. The minimum inhibitory concentration of APT2122 was 0.008 mg/ml, 0.016 mg/ml, 0.008 mg/ml, and 0.016 mg/ml for each microorganism respectively.

Example 25

Synthesis of APT2237 Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-[(S-2-thioethyl-succinyl-vancomycin vancosaminide)-Cys]—NH2 (Structure 16)

APT2237 was synthesised using the same overall methodology as used in Example 24. The most significant difference is the replacement of APT542 with APT2235, to give the structure shown. Retention time 14.1 min; The antibacterial activity of APT2237 was also determined against *E. faecium* STR 207, *E. faecalis* V 583, *E. faecium* STR 211, and *S. aureus* H, as described in Methods. The minimum inhibitory concentration of APT2237 was 0.016 mg/ml, 0.064 mg/ml, 0.016 mg/ml, and 0.008 mg/ml for each microorganism respectively.

SUMMARY OF BIOLOGICAL RESULTS

The antibacterial activities measured above are summarised in the following table, where all entries represent the maximum inhibitory composition, expressed in mg/ml.

|  | *E. faecium* STR 207 | *E. faecalis* V583 | *E. faecium* STR 211 | *S. aureus* H |
|---|---|---|---|---|
| APT 542 | 0.064 | 0.256 | 0.032 | 0.064 |
| APT 541 | 0.128 | 0.256 | 0.064 | 0.064 |
| APT 2033 | 0.256 | 0.032 | 0.002 | 0.004 |
| APT 2035 | 0.128 | 0.016 | 0.002 | 0.008 |
| APT 2036 | 0.008 | 0.008 | 0.008 | 0.004 |
| APT 2037 | 0.016 | 0.016 | 0.004 | 0.008 |
| APT 2038 | 0.064 | 0.064 | 0.002 | 0.008 |
| APT 2039 | 0.128 | 0.128 | 0.002 | 0.0016 |
| APT 2116 | 0.512 | 0.256 | 0.032 | >0.512 |
| APT 2117 | >0.512 | 0.512 | 0.008 | 0.008 |
| APT 2122 | 0.008 | 0.016 | 0.008 | 0.016 |
| APT 2208 | 0.008 | 0.016 | 0.002 | 0.004 |
| APT 2041 | 0.016 | 0.016 | 0.004 | 0.008 |
| APT 2209 | 0.032 | 0.064 | 0.016 | 0.032 |
| APT 2210 | 0.128 | 0.128 | 0.032 | >0.128 |
| APT 2211 | 0.008 | 0.032 | <0.00003 | 0.00025 |
| APT 2212 | 0.008 | 0.016 | 0.008 | 0.016 |
| APT 2237 | 0.016 | 0.064 | 0.016 | 0.008 |

| TABLE OF CHEMICAL STRUCTURES |
|---|

Structures 1–12

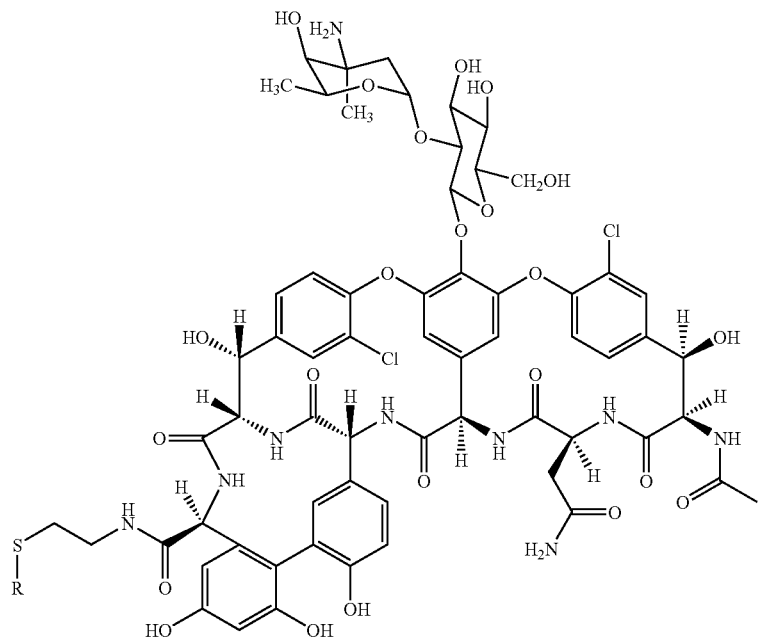

Structure 1: APT 2033 R = 2-thiopyridyl

Structure 2: APT 2035 R = H

Structure 3: APT 2036 R = Myristoyl-SEQ ID NO: 1-NH2

Structure 4: APT 2037 R = Lauroyl-SEQ ID NO: 1-NH2

Structure 5: APT 2038 R = Decanoyl-SEQ ID NO: 1-NH2

Structure 6: APT 2039 R = Octanoyl-SEQ ID NO: 1-NH2

Structure 7: APT 2040 R = n-Butyl-SEQ ID NO: 1-NH2

Structure 8: APT 2041 R = Myristoyl-SEQ ID NO: 2-NH2

Structure 9: APT 2208 R = Palmitoyl-SEQ ID NO: 1-NH2

Structure 10: APT 2209 R = Octadecanoyl-SEQ ID NO: 1-NH2

Structure 11: APT 2210 R = Eicosanoyl-SEQ ID NO: 1-NH2

Structure 12: APT 2211 R = N-(4-Biphenylcarboxyl)-SEQ ID NO: 1-NH2

TABLE OF CHEMICAL STRUCTURES

Structures 13–16:

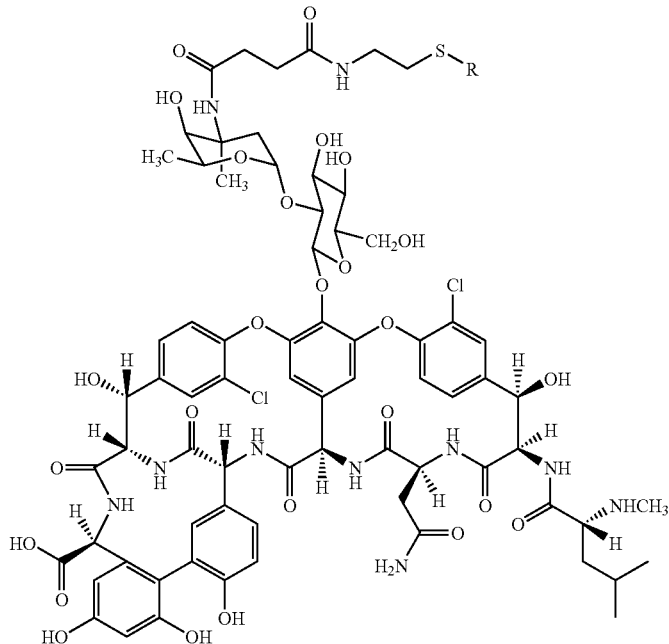

Structure 13: APT 2116 R = 2-thiopyridyl
Structure 14: APT 2117 R = H
Structure 15: APT 2122 R = Myristoyl-SEQ ID NO: 1-NH2
Structure 16: APT 2237 R = SEQ ID NO: 3-NH2

SEQUENCE LISTING

| Sequence | ID |
|---|---|
| GSSKSPSKKKKKKPGDC | SEQ ID NO:1 |
| GSSKSPSKDKDKDPGDC | SEQ ID NO:2 |
| GIGAVLKVLTTGLPALISWIKRKRQQC | SEQ ID NO:3 |
| DGPKKKKKKSPSKSSG | SEQ ID NO:4 |
| GSSKSPSKKKKKKPGD | SEQ ID NO:5 |
| SPSNETPKKKKKRFSFKKSG | SEQ ID NO:6 |
| DGPKKKKKKSPSKSSK | SEQ ID NO:7 |
| SKDGKKKKKKSKTK | SEQ ID NO:8 |
| GIGKFLHSAGKFGKAFVGEIMK | SEQ ID NO:9 |
| GIGKFLHSAKKFGKAFVGEIMNS | SEQ ID NO:10 |
| VGALAVVVWLWLW | SEQ ID NO:11 |
| GLLSVLGSVAKHVLPHVVPVIAEHL | SEQ ID NO:12 |
| FLGGLIKIVPAMICAVTKKC | SEQ ID NO:13 |
| GLFGVLAKVAAHVVPAIAEHF | SEQ ID NO:14 |
| VKLKVYPLKVKLYP | SEQ ID NO:15 |
| ILPWKWPWWPWRR | SEQ ID NO:16 |
| cyclized isooctanoyl BTBB (BFdLBBT) | SEQ ID NO:17 |
| KWKSFIKKLTSAAKKVVTTAKPLISS | SEQ ID NO:18 |
| KWKLFKKIGIGAVLKVLTTGLPALTLTK | SEQ ID NO:19 |
| KWKSFIKKLTTAVKKVLTTGLPALIS | SEQ ID NO:20 |
| ILKKPWWPWRRK-NH2 | SEQ ID NO:21 |
| KWKLFKKIGIGAVLKVLTTGLPALIS | SEQ ID NO:22 |
| Cyclized RL (CRIVVIRVC)R | SEQ ID NO:23 |
| RLCRIVVIRVCR | SEQ ID NO:24 |
| RLSRIVVIRVSR | SEQ ID NO:25 |
| cyclic (PFdLOVPFdLOV) | SEQ ID NO:26 |
| cyclic (PVKLKVdYdPLKVKLYd) | SEQ ID NO:27 |
| ILPWKWPWWPWRR-NH2 | SEQ ID NO:28 |
| GIGAVLKVLTTGLPALISWIKRKRQQ | SEQ ID NO:29 |
| GIGAdVLKdVLTTGLPALdISWIdKRKRQQ | SEQ ID NO:30 |
| GIGKFLKKAKKFGKAFVKILKK | SEQ ID NO:31 |
| GIGKFLHSAKKFGKAFVAEIMNS | SEQ ID NO:32 |

-continued
SEQUENCE LISTING

| | |
|---|---|
| GIAKFLHSAKKFGKAFVAEIMNS | SEQ ID NO:33 |
| AAGKFLHSAKKFGKAFVGDIMNS | SEQ ID NO:34 |
| G-GKFLHSAKKFGKAFVGEIMNS | SEQ ID NO:35 |
| G-GKFIHSAKKFGKAFVGEIMNS | SEQ ID NO:36 |

-continued
SEQUENCE LISTING

| | |
|---|---|
| GIGKFIHSAKKFGKAFVGEIMNSK | SEQ ID NO:37 |
| GIGAVLKVLTTGLPALISWIKRKRQQC | SEQ ID NO:38 |
| L-Alanine-γ-D-Glutamate-Xaa-D-Alanine-D-Alanine | SEQ ID NO:39 |

What is claimed is:

1. An antibacterial compound of formula V-L-W-X; wherein:

V is a glycopeptide moiety which inhibits peptidoglycan biosynthesis in bacteria;

L is a linking group;

W is a peptidic membrane-associating element and is either a membrane binding peptide including at least one sequence $(Xaa)_n$, where n is from 1 to 12 and each Xaa is independently lysine or arginine, and having an overall positive charge; or a membrane-inserting peptide;

X is a membrane-insertive element and is a lipophilic chain wherein the lipophilic chain is described as:

having from 6 to 30 carbon atoms including those of any aromatic rings;

straight or branched containing one to three branch points;

saturated or unsaturated containing one to four double or triple bonds;

optionally having 1, 2 or 3 heteroatoms (in addition to those in any aromatic rings) independently selected from the group consisting of S, O and N;

optionally containing one or more aromatic rings, which may be fused and each of which may contain from 1, 2 or 3 heteroatoms independently selected from the group consisting of N, O and S; and optionally having from one to three substituents selected from the group consisting of hydroxy, -SH, amino and halo; and V-L- is of the formula:

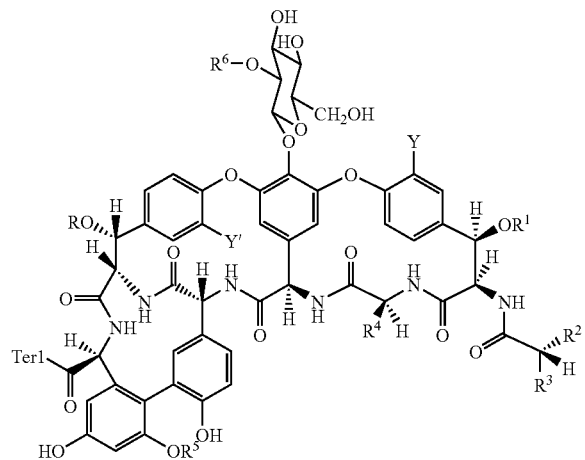

wherein:

Y and Y' are independently hydrogen or chloro;

R is selected from the group consisting of hydrogen, 4-epi-vancosaminyl, actinosaminyl, and ristosaminyl, or R is a group of the formula —$R^a$-L- wherein $R^a$ is selected from the group consisting of 4-epi-vancosaminyl, actinosaminyl, and ristosaminyl and L is attached to the amino group of $R^a$;

$R^1$ is hydrogen or mannose;

$R^2$ is selected from the group consisting of —$NH_2$, —$NHCH_3$, —$N(CH_3)_2$, —NHL-, and —$N(CH_3)$L-;

$R^3$ is selected from the group consisting of —$CH_2CH(CH_3)_2$, [p-OH, m-Cl]phenyl, p-rhamnose-phenyl, [p-rhamnose-galactose]phenyl, [p-galactose-galactose]phenyl, and [p-$CH_3$O-rhamnose]phenyl;

$R^4$ is selected from the group consisting of —$CH_2$—(CO)$NH_2$, benzyl, [p-OH]phenyl, and [p-OH, m-Cl]phenyl;

$R^5$ is hydrogen or mannose, $R^6$ is selected from the group consisting of hydrogen, 4-epi-vancosaminyl, vancosaminyl, actinosaminyl, ristosaminyl, or acosaminyl; or $R^6$ is a group of the formula $R^b$-L- wherein $R^b$ is selected from the group consisting of 4-epi-vancosaminyl, vancosaminyl, actinosaminyl, ristosaminyl and acosaminyl and L is attached to the amino group of $R^b$; or $R^6$ is a group $R^b$—$R^7$ wherein $R^b$ is selected from the group consisting of 4-epi-vancosaminyl, vancosaminyl, actinosaminyl, ristosaminyl and acosaminyl and $R^7$ is an organic side chain moiety which is no more than 1000 Da; and Ter1 is hydroxy or -L-, provided that the compound includes at least one group -L-.

2. A compound according to claim 1 wherein $R^6$ is a group $R^b$—$R^7$ wherein $R^b$ is selected from the group consisting of 4-epi-vancosaminyl, vancosaminyl, actinos-aminyl, ristosaminyl and acosaminyl and $R^7$ includes those of the formula —$CH_2$—$R^8$, in which $R^8$ is selected from the group consisting of hydrogen, $C_1$–$C_{15}$ alkyl, $C_2$–$C_{15}$ alkenyl, $C_2$–$C_{15}$ alkynyl, $C_1$–$C_7$ haloalkyl, acenaphthenyl, 2-fluorenyl, 9,10-dihydro-2-phenanthrenyl, $R^9$, $C_1$–$C_{11}$ alkyl-$R^9$, $C_2$–$C_7$ alkenyl-$R^9$, $C_2$–$C_7$ alkynyl-$R^9$, and $C_1$–$C_7$ alkyl-O—$R^9$ wherein $R^9$ is a radical of the formula:

—$R^{10}$-[linker$_{(0\ or\ 1)}$—$R^{10}$]$_{(0\ or\ 1)}$ wherein each $R^{10}$ is independently selected from the group consisting of phenyl, $C_5$–$C_6$ cycloalkyl, naphthyl, and thienyl, each of which is unsubstituted or is optionally substituted with one or two substituents independently selected from the group consisting of $C_1$–$C_{10}$ alkyl, $C_1$–$C_2$ haloalkyl, $C_1$–$C_2$ haloalkoxy, $C_1$–$C_{10}$ alkoxy, halo, cyano, and nitro;

and "linker" is selected from the group consisting of $C_1$–$C_3$-alkylene, —O—$C_1$–$C_6$ alkylene, $C_1$–$C_6$-alkylene-O—, —O—, —N(H or $C_1$–$C_3$ lower alkyl)-, —S—, —SO—, —$S_2$—, —NH—C(O)—, —C(O)—NH—, —CH=CH—, —C≡C—, —N=N—, —O—C(O)—, and —C(O)—O—.

3. A compound according to any one of the preceding claims wherein V is selected from the group consisting of vancomycin, chloroeremomycin, teicoplanin, $A_2$-2, ristocetin A, eremomycin, balkimycin, actinodin A, complestanin, chloropeptin 1, kistamycin A, and avoparcin.

4. A compound according to any one of the preceding claims wherein W is a membrane-binding peptide comprising from 2 to 10 contiguous residues selected from lysine and arginine.

5. A compound according to claim 4 wherein the membrane-binding peptide comprises from 7 to 30 amino acids.

6. A compound according to claim 4 wherein the membrane-binding peptide is selected from the group consisting of:

DGPKKKKKKSPSKSSG (SEQ ID NO: 4);
GSSKSPSKKKKKKPGD (SEQ ID NO: 5);
SPSNETPKKKKKKRFSFKKSG (SEQ ID NO: 6);
DGPKKKKKKSPSKSSK (SEQ ID NO: 7); and
SKDGKKKKKKSKTK (SEQ ID NO: 8).

7. A compound according to claim 1 wherein W is a membrane-inserting peptide selected from the group consisting of α-defensins, β-defensins, and bacteriocins.

8. A compound according to claim 7 wherein said β-defensin is a tachyplesin.

9. A compound according to claim 1 wherein said membrane-inserting peptide is a magainin.

10. A compound according to claim 1 wherein said membrane-inserting peptide is maculatin 1.1 or caerin 1.1.

11. A method of treating a bacterial infection in a subject which method comprises administering to said subject an effective amount of the antibacterial agent of claim 1.

12. A composition comprising a compound according to claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,078,380 B2 | |
| APPLICATION NO. | : 10/415935 | |
| DATED | : July 18, 2006 | |
| INVENTOR(S) | : Matthew Allister Cooper et al. | |

It is certified that error appears in the above-identified patent and that said Letters Patent is hereby corrected as shown below:

Title Page: Item (54)
Please replace "MEMBRANE ASSOCIATING" with --MEMBRANE-ASSOCIATING-- in the title of the invention.

Column 1, line 3:
Please replace "MEMBRANE ASSOCIATING" with --MEMBRANE-ASSOCIATING-- in the title of the invention.

Column 1, line 26:
Please replace "Host" with --host--.

Column 2, line 5:
Please replace "pply-" with --poly- --.

Column 5, line 27:
Please replace "otics. have" with --otics have--.

Column 8, line 52:
Please replace "-alkylene of C1-C6," with -- -alkylene of C1-C6-O-,--

Column 49, lines 60-61 (claim 1):
Please replace "or a membrane-inserting peptide;" with --or a membrane-inserting peptide selected from the group consisting of α-defensins, β-defensins, bactericins, a magainin, maculatin 1.1, and caerin 1.1;--.

Column 52, line 14 (claim 2):
Please replace "-$R^{10}$-[linker$_{(0 \text{ or } 1)}$-$R^{10}$]$_{(0 \text{ or } 1)}$" with
-- -$R^{10}$-[linker$_{(0 \text{ or } 1)}$-$R^{10}$]$_{(0 \text{ or } 1)}$--.

Column 52, line 25 (claim 2):
Please replace "-$S_2$-" with -- -$SO_2$- --.

Column 52, lines 28-29 (claim 3):
Please replace "any one of the preceding claims" with --claim 1--.

UNITED STATES PATENT AND TRADEMARK OFFICE
CERTIFICATE OF CORRECTION

PATENT NO. : 7,078,380 B2
APPLICATION NO. : 10/415935
DATED : July 18, 2006
INVENTOR(S) : Matthew Allister Cooper et al.

It is certified that error appears in the above-identified patent and that said Letters Patent is hereby corrected as shown below:

Column 52, lines 33-34 (claim 4):
Please replace "any one of the preceding claims" with --claim 1--.

Signed and Sealed this

Twenty-sixth Day of December, 2006

JON W. DUDAS
*Director of the United States Patent and Trademark Office*

SEQUENCE LISTING

<160> NUMBER OF SEQ ID NOS: 39

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic

<400> SEQUENCE: 1

Gly Ser Ser Lys Ser Pro Ser Lys Lys Lys Lys Lys Pro Gly Asp
 1               5                  10                  15

Cys

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic

<400> SEQUENCE: 2

Gly Ser Ser Lys Ser Pro Ser Lys Asp Lys Asp Lys Asp Pro Gly Asp
 1               5                  10                  15

Cys

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic

<400> SEQUENCE: 3

Gly Ile Gly Ala Val Leu Lys Val Leu Thr Thr Gly Leu Pro Ala Leu
 1               5                  10                  15

Ile Ser Trp Ile Lys Arg Lys Arg Gln Gln Cys
            20                  25

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence:
      Membrane-binding peptide

```
<400> SEQUENCE: 4

Asp Gly Pro Lys Lys Lys Lys Lys Ser Pro Ser Lys Ser Ser Gly
 1               5                  10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence:
      Membrane-binding peptide

<400> SEQUENCE: 5

Gly Ser Ser Lys Ser Pro Ser Lys Lys Lys Lys Lys Pro Gly Asp
 1               5                  10                  15

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence:
      Membrane-binding peptide

<400> SEQUENCE: 6

Ser Pro Ser Asn Glu Thr Pro Lys Lys Lys Lys Arg Phe Ser Phe
 1               5                  10                  15

Lys Lys Ser Gly
            20

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence:
      Membrane-binding peptide

<400> SEQUENCE: 7

Asp Gly Pro Lys Lys Lys Lys Lys Ser Pro Ser Lys Ser Ser Lys
 1               5                  10                  15

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence:
      Membrane-binding peptide

<400> SEQUENCE: 8

Ser Lys Asp Gly Lys Lys Lys Lys Lys Ser Lys Thr Lys
 1               5                  10

<210> SEQ ID NO 9
<211> LENGTH: 22
<212> TYPE: PRT
<213> ORGANISM: Xenopus laevis

<400> SEQUENCE: 9

Gly Ile Gly Lys Phe Leu His Ser Ala Gly Lys Phe Gly Lys Ala Phe
 1               5                  10                  15

Val Gly Glu Ile Met Lys
            20
```

```
<210> SEQ ID NO 10
<211> LENGTH: 23
<212> TYPE: PRT
<213> ORGANISM: Xenopus laevis

<400> SEQUENCE: 10

Gly Ile Gly Lys Phe Leu His Ser Ala Lys Lys Phe Gly Lys Ala Phe
 1               5                  10                  15

Val Gly Glu Ile Met Asn Ser
            20

<210> SEQ ID NO 11
<211> LENGTH: 15
<212> TYPE: PRT
<213> ORGANISM: Unknown Organism
<220> FEATURE:
<223> OTHER INFORMATION: Description of Unknown Organism: Eukaryotic:
      antibacterial peptide

<400> SEQUENCE: 11

Val Gly Ala Leu Ala Val Val Trp Leu Trp Leu Trp Leu Trp
 1               5                  10                  15

<210> SEQ ID NO 12
<211> LENGTH: 25
<212> TYPE: PRT
<213> ORGANISM: Unknown Organism
<220> FEATURE:
<223> OTHER INFORMATION: Description of Unknown Organism: Eukaryotic:
      antibacterial peptide

<400> SEQUENCE: 12

Gly Leu Leu Ser Val Leu Gly Ser Val Ala Lys His Val Leu Pro His
 1               5                  10                  15

Val Val Pro Val Ile Ala Glu His Leu
            20                  25

<210> SEQ ID NO 13
<211> LENGTH: 20
<212> TYPE: PRT
<213> ORGANISM: Unknown Organism
<220> FEATURE:
<223> OTHER INFORMATION: Description of Unknown Organism: Eukaryotic:
      antibacterial peptide

<400> SEQUENCE: 13

Phe Leu Gly Gly Leu Ile Lys Ile Val Pro Ala Met Ile Cys Ala Val
 1               5                  10                  15

Thr Lys Lys Cys
            20

<210> SEQ ID NO 14
<211> LENGTH: 21
<212> TYPE: PRT
<213> ORGANISM: Unknown Organism
<220> FEATURE:
<223> OTHER INFORMATION: Description of Unknown Organism: Eukaryotic:
      antibacterial peptide

<400> SEQUENCE: 14

Gly Leu Phe Gly Val Leu Ala Lys Val Ala Ala His Val Val Pro Ala
 1               5                  10                  15

Ile Ala Glu His Phe
            20
```

```
<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 15

Val Lys Leu Lys Val Tyr Pro Leu Lys Val Lys Leu Tyr Pro
 1               5                  10

<210> SEQ ID NO 16
<211> LENGTH: 13
<212> TYPE: PRT
<213> ORGANISM: Unknown Organism
<220> FEATURE:
<223> OTHER INFORMATION: Description of Unknown Organism: Eukaryotic:
      antibacterial peptide

<400> SEQUENCE: 16

Ile Leu Pro Trp Lys Trp Pro Trp Trp Pro Trp Arg Arg
 1               5                  10

<210> SEQ ID NO 17
<211> LENGTH: 10
<212> TYPE: PRT
<213> ORGANISM: Unknown Organism
<220> FEATURE:
<223> OTHER INFORMATION: Description of Unknown Organism: Eukaryotic:
      antibacterial peptide
<220> FEATURE:
<223> OTHER INFORMATION: Cyclized isooctanoyl
<220> FEATURE:
<221> NAME/KEY: SITE
<222> LOCATION: (1, 3..5, 8, 9)
<223> OTHER INFORMATION: Xaa is diaminobenzoate
<220> FEATURE:
<221> NAME/KEY: SITE
<222> LOCATION: (7)
<223> OTHER INFORMATION: Xaa is d-Leu

<400> SEQUENCE: 17

Xaa Thr Xaa Xaa Xaa Phe Xaa Xaa Xaa Thr
 1               5                  10

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: Synthetic

<400> SEQUENCE: 18

Lys Trp Lys Ser Phe Ile Lys Lys Leu Thr Ser Ala Ala Lys Lys Val
 1               5                  10                  15

Val Thr Thr Ala Lys Pro Leu Ile Ser Ser
            20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 19

Lys Trp Lys Leu Phe Lys Lys Ile Gly Ile Gly Ala Val Leu Lys Val
 1               5                  10                  15
```

Leu Thr Thr Gly Leu Pro Ala Leu Thr Leu Thr Lys
            20                  25

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic

<400> SEQUENCE: 20

Lys Trp Lys Ser Phe Ile Lys Lys Leu Thr Thr Ala Val Lys Lys Val
  1               5                  10                  15

Leu Thr Thr Gly Leu Pro Ala Leu Ile Ser
            20                  25

<210> SEQ ID NO 21
<211> LENGTH: 13
<212> TYPE: PRT
<213> ORGANISM: Artificial Sequence
<220> FEATURE:
<221> NAME/KEY: MOD_RES
<222> LOCATION: (13)
<223> OTHER INFORMATION: AMIDATION
<220> FEATURE:
<223> OTHER INFORMATION: Description of Artificial Sequence: Synthetic

<400> SEQUENCE: 21

Ile Leu Lys Lys Trp Pro Trp Trp Pro Trp Arg Arg Lys
  1               5                  10

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence: Synthetic

<400> SEQUENCE: 22

Lys Trp Lys Leu Phe Lys Lys Ile Gly Ile Gly Ala Val Leu Lys Val
  1               5                  10                  15

Leu Thr Thr Gly Leu Pro Ala Leu Ile Ser
            20                  25

<210> SEQ ID NO 23
<211> LENGTH: 12
<212> TYPE: PRT
<213> ORGANISM: Unknown Organism
<220> FEATURE:
<223> OTHER INFORMATION: Description of Unknown Organism: Eukaryotic:
      antibacterial peptide
<220> FEATURE:
<223> OTHER INFORMATION: Cyclized

<400> SEQUENCE: 23

Arg Leu Cys Arg Ile Val Val Ile Arg Val Cys Arg
  1               5                  10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 24

-continued

```
Arg Leu Cys Arg Ile Val Val Ile Arg Val Cys Arg
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 25

Arg Leu Ser Arg Ile Val Val Ile Arg Val Ser Arg
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (3, 8)
<223> OTHER INFORMATION: Xaa is d-Leu
<220> FEATURE:
<221> NAME/KEY: MOD_RES
<222> LOCATION: (4, 9)
<223> OTHER INFORMATION: Orn
<220> FEATURE:
<223> OTHER INFORMATION: Cyclic

<400> SEQUENCE: 26

Pro Phe Xaa Xaa Val Pro Phe Xaa Xaa Val
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
<220> FEATURE:
<223> OTHER INFORMATION: Cyclic
<220> FEATURE:
<221> NAME/KEY: SITE
<222> LOCATION: (1, 8)
<223> OTHER INFORMATION: Xaa is d-Pro
<220> FEATURE:
<221> NAME/KEY: SITE
<222> LOCATION: (7)
<223> OTHER INFORMATION: Xaa is d-Tyr

<400> SEQUENCE: 27

Xaa Val Lys Leu Lys Val Xaa Xaa Leu Lys Val Lys Leu Tyr
1               5                   10

<210> SEQ ID NO 28
<211> LENGTH: 13
<212> TYPE: PRT
<213> ORGANISM: Unknown Organism
<220> FEATURE:
<223> OTHER INFORMATION: Description of Unknown Organism: Eukaryotic:
      antibacterial peptide
<220> FEATURE:
<221> NAME/KEY: MOD_RES
<222> LOCATION: (13)
<223> OTHER INFORMATION: AMIDATION

<400> SEQUENCE: 28

Ile Leu Pro Trp Lys Trp Pro Trp Trp Pro Trp Arg Arg
1               5                   10
```

-continued

<210> SEQ ID NO 29
<211> LENGTH: 26
<212> TYPE: PRT
<213> ORGANISM: Unknown Organism
<220> FEATURE:
<223> OTHER INFORMATION: Description of Unknown Organism: Eukaryotic:
      antibacterial peptide

<400> SEQUENCE: 29

Gly Ile Gly Ala Val Leu Lys Val Leu Thr Thr Gly Leu Pro Ala Leu
 1               5                  10                  15

Ile Ser Trp Ile Lys Arg Lys Arg Gln Gln
            20                  25

<210> SEQ ID NO 30
<211> LENGTH: 26
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (5, 8)
<223> OTHER INFORMATION: Xaa is d-Val
<220> FEATURE:
<221> NAME/KEY: SITE
<222> LOCATION: (17)
<223> OTHER INFORMATION: Xaa is d-Ile
<220> FEATURE:
<221> NAME/KEY: SITE
<222> LOCATION: (21)
<223> OTHER INFORMATION: Xaa is d-Lys

<400> SEQUENCE: 30

Gly Ile Gly Ala Xaa Leu Lys Xaa Leu Thr Thr Gly Leu Pro Ala Leu
 1               5                  10                  15

Xaa Ser Trp Ile Xaa Arg Lys Arg Gln Gln
            20                  25

<210> SEQ ID NO 31
<211> LENGTH: 22
<212> TYPE: PRT
<213> ORGANISM: Unknown Organism
<220> FEATURE:
<223> OTHER INFORMATION: Description of Unknown Organism: Eukaryotic:
      antibacterial peptide

<400> SEQUENCE: 31

Gly Ile Gly Lys Phe Leu Lys Lys Ala Lys Lys Phe Gly Lys Ala Phe
 1               5                  10                  15

Val Lys Ile Leu Lys Lys
            20

<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence:
      Membrane-inserting peptide

<400> SEQUENCE: 32

Gly Ile Gly Lys Phe Leu His Ser Ala Lys Lys Phe Gly Lys Ala Phe
 1               5                  10                  15

Val Ala Glu Ile Met Asn Ser
            20

<210> SEQ ID NO 33
<211> LENGTH: 23
<212> TYPE: PRT
<213> ORGANISM: Artificial Sequence
<220> FEATURE:
<223> OTHER INFORMATION: Description of Artificial Sequence:
    Membrane-inserting peptide

<400> SEQUENCE: 33

Gly Ile Ala Lys Phe Leu His Ser Ala Lys Lys Phe Gly Lys Ala Phe
 1               5                  10                  15

Val Ala Glu Ile Met Asn Ser
            20

<210> SEQ ID NO 34
<211> LENGTH: 23
<212> TYPE: PRT
<213> ORGANISM: Artificial Sequence
<220> FEATURE:
<223> OTHER INFORMATION: Description of Artificial Sequence:
    Membrane-inserting peptide

<400> SEQUENCE: 34

Ala Ala Gly Lys Phe Leu His Ser Ala Lys Lys Phe Gly Lys Ala Phe
 1               5                  10                  15

Val Gly Asp Ile Met Asn Ser
            20

<210> SEQ ID NO 35
<211> LENGTH: 22
<212> TYPE: PRT
<213> ORGANISM: Artificial Sequence
<220> FEATURE:
<223> OTHER INFORMATION: Description of Artificial Sequence:
    Membrane-inserting peptide

<400> SEQUENCE: 35

Gly Gly Lys Phe Leu His Ser Ala Lys Lys Phe Gly Lys Ala Phe Val
 1               5                  10                  15

Gly Glu Ile Met Asn Ser
            20

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence:
    Membrane-inserting peptide

<400> SEQUENCE: 36

Gly Gly Lys Phe Ile His Ser Ala Lys Lys Phe Gly Lys Ala Phe Val
 1               5                  10                  15

Gly Glu Ile Met Asn Ser
            20

<210> SEQ ID NO 37
<211> LENGTH: 24
<212> TYPE: PRT
<213> ORGANISM: Artificial Sequence
<220> FEATURE:

```
<223> OTHER INFORMATION: Description of Artificial Sequence:
      Membrane-inserting peptide

<400> SEQUENCE: 37

Gly Ile Gly Lys Phe Ile His Ser Ala Lys Lys Phe Gly Lys Ala Phe
 1               5                  10                  15

Val Gly Glu Ile Met Asn Ser Lys
            20

<210> SEQ ID NO 38
<211> LENGTH: 27
<212> TYPE: PRT
<213> ORGANISM: Artificial Sequence
<220> FEATURE:
<223> OTHER INFORMATION: Description of Artificial Sequence:
      Membrane-inserting peptide

<400> SEQUENCE: 38

Gly Ile Gly Ala Val Leu Lys Val Leu Thr Thr Gly Leu Pro Ala Leu
 1               5                  10                  15

Ile Ser Trp Ile Lys Arg Lys Arg Gln Gln Cys
            20                  25

<210> SEQ ID NO 39
<211> LENGTH: 5
<212> TYPE: PRT
<213> ORGANISM: Unknown Organism
<220> FEATURE:
<223> OTHER INFORMATION: Description of Unknown Organism: Bacterial:
      Pentapeptide precursor of peptidoglycan
<220> FEATURE:
<221> NAME/KEY: SITE
<222> LOCATION: (2)
<223> OTHER INFORMATION: Xaa is gamma-d-Glutamate
<220> FEATURE:
<221> NAME/KEY: SITE
<222> LOCATION: (3)
<223> OTHER INFORMATION: Xaa is usually m-D-amino pimelic acid but in
      some species (e.g. S. aureus) is L-lysine
<220> FEATURE:
<221> NAME/KEY: SITE
<222> LOCATION: (4)..(5)
<223> OTHER INFORMATION: Xaa is d-Ala

<400> SEQUENCE: 39

Ala Xaa Xaa Xaa Xaa
 1               5
```